US007749772B1

(12) United States Patent
Wang

(10) Patent No.: US 7,749,772 B1
(45) Date of Patent: Jul. 6, 2010

(54) ANTIBODY AND IMMUNOASSAYS FOR DETERMINING THE PRESENCE OF $\Delta^9$-TETRAHYDROCANNABINOL

(75) Inventor: Daniel Wang, San Diego, CA (US)

(73) Assignee: Varian, Inc., Palo Alto, CA (US)

( * ) Notice: Subject to any disclaimer, the term of this patent is extended or adjusted under 35 U.S.C. 154(b) by 495 days.

(21) Appl. No.: 11/478,972

(22) Filed: Jun. 29, 2006

(51) Int. Cl.
*A61K 35/14* (2006.01)

(52) U.S. Cl. .................... 436/514; 530/386; 530/387.1; 530/387.9; 530/388.1; 530/388.15; 436/547; 436/548; 436/518; 436/810; 435/7.1; 435/7.91

(58) Field of Classification Search ........................ None
See application file for complete search history.

(56) References Cited

U.S. PATENT DOCUMENTS

| 4,275,149 | A | 6/1981 | Litman et al. |
| 4,542,104 | A | 9/1985 | Stryer et al. |
| 5,183,740 | A | 2/1993 | Ligler et al. |
| 5,264,373 | A | 11/1993 | Wang et al. |
| 5,541,113 | A | 7/1996 | Siddigi et al. |
| 5,770,458 | A | 6/1998 | Klimov et al. |
| 6,001,658 | A | 12/1999 | Fredrickson |
| 6,368,876 | B1 | 4/2002 | Huang et al. |
| 6,468,474 | B2 | 10/2002 | Bachand et al. |
| 6,686,208 | B2 | 2/2004 | Meusel et al. |
| 6,719,971 | B1 | 4/2004 | Carter et al. |
| 6,800,738 | B1 | 10/2004 | Carter et al. |
| 2003/0022240 | A1 | 1/2003 | Luo et al. |
| 2004/0133357 | A1 | 7/2004 | Zhong et al. |
| 2006/0057027 | A1 | 3/2006 | Hudak et al. |
| 2006/0122377 | A1 | 6/2006 | Dennis |

FOREIGN PATENT DOCUMENTS

| WO | WO 86/02734 | 5/1986 |
| WO | WO 90/05296 | 5/1990 |

OTHER PUBLICATIONS

Mikayama et al., Proc. Natl. Acad. Sci. USA. vol. 90, pp. 10056-10060. Nov. 1993.*
Rudinger et al., Peptide Hormones. Biol. Countil. pp. 5-7. Jun. 1976.*
Rudikoff et al., Proc. Natl. Acad. Sci. USA. vol. 79. p. 1979-1982.*
Altschul, S.F. , "Amino acid substitution matrices from an information theoretic perspective," Journal of Molecular Biology (1991), 219, 555-565.
Dayhoff, M.O., et al. "A model of evolutionary change in proteins," Atlas of Protein Sequence and Structure, 1978, 345-352.
Dayhoff, M.O.,"Transfer RNA", Atlas of Protein Sequence and Structure, 1972, D-345-D352, National Biomedical Research Foundation, Washington.
States, D.J., et al., "Improved Sensitivity of Nucleic Acid Database Search Using Application-Specific Scoring Matrices," Methods: A companion to Methods in Enzymology, vol. 3, No. 1, Aug. 66-70, 1991.
Henikoff, Steven et al., "Amino acid substitution matrices from protein blocks," Proc. Natl. Acad. Sci. USA, vol. 89, 10915-10919, Nov. 1992.
Johnson, MS et. al., "A Structural Basis of Sequence Comparisons: An evaluation of scoring methodologies," J. Mol. Biol. (1993), 233, 716-738.
Henikoff, Steven et al., "Performance Evaluation of Amino Acid Substitution Matrices", Proteins: Structure, Function, and Genetics 17, 49-61, (1993).
Current Protocols in Immunology, vols. 1 and 2, Coligen et al., Ed., Wiley-Interscience, New York, N.Y., Pubs. (1991).
Persoon, Thomas, "Immunochemical Assays in the Clinical Laboratory", vol. 5, No. 1 Jan./Feb. 1992 Clinical Laboratory Science, 31-34.
Stites, Daniel P., et al., Basic and Clinical Immunology, Appleton & Lange, Norwalk, Connecticut, 1994.
Hemmila, Ilkka, "Fluoroimmunoassays and Immunofluorometric Assays", Clinical Chemistry, vol. 31, No. 3., 1985, 359-370.
Leland, JK, et al., "Electrogenerated Chemiluminescence: An Oxidative-Reduction Type ECL Reactions Sequence Using Triprophyl Amine", J. Electrochem. Soc., vol. 137, No. 10, Oct. 1990, The Elctrochemical Society, Inc. 3127-3131.
Remington's Pharmaceutical Sciences 16th edition, Osol, A. Ed. (1980).
Kemeny, DM, et al., "ELISA and Other Solid Phase Immunoassays", (1988).

\* cited by examiner

*Primary Examiner*—Bao-Thuy L Nguyen
(74) *Attorney, Agent, or Firm*—Bella Fishman; Cynthia R. Moore

(57) ABSTRACT

Antibodies having specific binding for the parent THC ($\Delta^9$-THC) and its major metabolites are provided which present a significant increase in sensitivity of immunoassays such as lateral flow immunoassays and ELISA for THC. The present invention also provides a rabbit hybridoma producing the antibody as a monoclonal antibody, a recombinant antibody, further molecularly engineered recombinant antibodies against parent $\Delta^9$-THC and its metabolites and cell lines producing the recombinant antibodies. The invention also provides applications of the antibody in immunoassays, particularly lateral flow immunoassays, specifically applications in detecting THC in body fluids, particularly saliva, and kits for determining the presence of THC.

13 Claims, No Drawings

ANTIBODY AND IMMUNOASSAYS FOR DETERMINING THE PRESENCE OF Δ⁹-TETRAHYDROCANNABINOL

FIELD OF THE INVENTION

This invention relates generally to immunoassays for drugs of abuse and the like.

BACKGROUND OF THE INVENTION

Marijuana is a member of the hemp family and is known to contain significant amounts of cannabinoids. In particular, the most important cannabinoid is $\Delta^9$-Tetrahydrocannabinol ($\Delta^9$-THC), the major physiologically active constituent of marijuana. $\Delta^9$-THC is a controlled substance because it has both sedative and depressant-like effects on the cardiovascular and central nervous systems, as opposed to cannabidiol, a non-psychoactive constituent of marijuana. Through smoking marijuana, $\Delta^9$-THC is rapidly absorbed from the lungs into the blood stream and metabolized through 11-nor$\Delta^9$-THC to a series of polar metabolites with 11-nor-$\Delta^9$-THC-carboxylic acid as the primary metabolite.

Due to the common abuse of cannabinoids, there is a need for non-invasive and rapid tests to detect the presence of these controlled drugs in biological specimens. Currently, cannabinoids in biological samples can be detected by a number of techniques such as thin layer chromatography (TLC), gas chromatography/mass spectrometry (GC/MS), radioimmunoassay, enzyme immunoassay or continuous flow displacement immunoassay (U.S. Pat. No. 6,686,208). Depending upon assay sensitivity, cannabinoid metabolites may be detected in the urine for up to 10 days in occasional smokers and 36 days in chronic smokers. See U.S. Pat. No. 5,264,373.

Tetrahydrocannabinol, the active ingredient in the marijuana plant (cannabis sativa), is detectable in saliva shortly after use. The detection of the drug in saliva is thought to be primarily due to the direct exposure of the drug to the mouth (oral and smoking administrations) and the subsequent sequestering of the drug in the buccal cavity. The non-metabolized drug, $\Delta^9$-THC is the main form of THC present in the marijuana smoker's oral fluid sample. Thus the presence of $\Delta^9$-THC in oral fluids is an excellent indicator of recent marijuana consumption and may indicate that the person is under the drug's influence. Detection of the parent THC therefore is of great interest for road side testing by law enforcement, on-site testing in work places and many other circumstances.

Previous studies have shown a time window of detection for THC in saliva of up to 14 hours after drug use. In recent years, there have been efforts to utilize saliva for drug monitoring for the presence of $\Delta^9$-THC, for pharmacokinetic studies or for the management of patients in chronic drug therapy. Although saliva testing does not quantify the blood concentration of the drug, saliva testing is of particular interest since the presence of $\Delta^9$-THC in the saliva is indicative of recent smoking of cannabinoids. The concentration of $\Delta^9$-THC in the blood is usually much higher than the drug concentration in saliva.

The use of saliva THC assays and procedures however are still problematic. Due to the short detectable time window of the parent THC in the oral fluid, low quantity, the low THC solubility and "stickiness" in aqueous solution, and sensitivity limitations of currently available murine anti-THC antibodies, current lateral flow immunoassays for parent THC can not meet the expected sensitivity requirement recommended by the Substance Abuse and Mental Health Services Administration (SAMHSA).

For example, the THC assay contained within the Oral Fluid Drug Screen Device (ORATECT® II, Branan Medical Corp., Irvine, Calif.) is purported to detect the presence of THC-COOH. However, this assay requires the presence of the THC metabolite THC-COOH, and does not detect the parent $\Delta^9$-THC molecule with a high sensitivity.

The THC "One Step Marijuana Test Strip" (Biomerica, Inc. Newport Beach, Calif.) is reported to be a rapid chromatographic immunoassay for the detection of 11-nor-9-THC-9 COOH in human urine at a cut-off concentration of 50 ng/mL. However, this assay system cannot be used to detect the parent $\Delta^9$-THC molecule in saliva and requires urine collection and testing.

A fluorescence immunoassay has been reported for the detection and quantitation of tetrahydrocannabinols in oral fluids for use in testing for marijuana abuse. The lower detection limits were reported to be 1.5 ng/mL for (1)-,9-THC and 5.5 ng/mL for (1)9-Carboxy-1'-nor-,9-THC and to require a total assay reaction time of less than 10 minutes. However, fluorescence detection is required for this assay, necessitating the use of expensive equipment and limiting the availability and widespread usage of this assay.

The use of a continuous flow displacement immunoassay technology (U.S. Pat. No. 5,183,740 to Ligler) has been demonstrated for detection of controlled drugs in saliva and urine. See also U.S. Pat. No. 6,686,208 to Wang. However, this assay procedure requires the use of a tracer molecule capable of binding to the same antigen or ligand binding site(s) of an antibody or receptor to $\Delta^9$-THC or its metabolites, to compete with $\Delta^9$-THC or its metabolites in an immunoassay, and the binding affinity of the antibody to the tracer molecules must be lower than the binding affinity of the antibody to the analyte to facilitate effective displacement. Using a $\Delta^9$-THC-based or $\Delta^9$-THC-analog based tracers is problematic because the $\Delta^9$-THC analyte does not effectively displace the $\Delta^9$-THC-based or $\Delta^9$-THC-analog based tracer. This results in a lower sensitivity of the assay.

There exist more sensitive immunoassay methods such as ELISA, however, there is a great need in the art for more sensitive assays and assay systems for ascertaining the presence of $\Delta^9$-THC that are inexpensive to prepare, purchase and operate, that operate in a noninvasive manner and that are easy to use for persons unskilled in laboratory assay procedures. To satisfy this need, more sensitive and specific antibodies for use in detecting $\Delta^9$-THC are required for use in lateral flow immunoassays. In particular, there is a need for a test comprising a sensitive and specific antibody having binding affinity for the parent $\Delta^9$-THC molecule, in order to detect the presence of the parent $\Delta^9$-THC molecule in saliva.

These and other deficiencies in the art are addressed by the invention described below.

SUMMARY OF THE INVENTION

Accordingly, it is a primary object of the invention to address the aforementioned need in the art by providing an antibody having specific binding for THC and its metabolites, wherein said antibody comprises CDR amino acid sequences selected from the group consisting of L1: QASQSVYNNNQLS (SEQ ID NO:1); L2: GTSNLAS (SEQ ID NO:2); L3: QGGYTSGDGIA (SEQ ID NO:3); H1: GFSLSNYVLA (SEQ ID NO:4); H2: TIVSGTTYYASW (SEQ ID NO:5); H3: GLPHYITGDI (SEQ ID NO:6) or homologous amino acid sequences having at least 85% homology thereto.

In certain embodiments, the amino acid sequence for the light chain variable region comprises the sequence: QVLTQTPSPVSAAVGGTVTINCQASQS-VYNNNQLSWYQQKPGQPPKLLIYGTSNLASG VPSR-FKGSGSGTQFTLTISSVQCDDAATYYC-QGGYTSGDGIAFGGGTEVVVK (SEQ ID NO:7), or homologous amino acid sequences having at least 85% homology thereto. In certain other embodiments, the amino acid sequence for the heavy chain variable region comprises the sequence: QSVEESGGRLVTPGTPLTLTCTVSGFSL-SNYVLAWVRQAPGKGLEWIGTIVSGTTYYAS WAKGRFTISKTSTTVHLKITSPTTED-TATYFCVRGLPHYITGDIWGPGTLVTVSLG (SEQ ID NO:8), or homologous amino acid sequences having at least 85% homology thereto.

In certain preferred embodiments, the antibody is a monoclonal antibody produced by a hybridoma. In additional preferred embodiments, the antibody is a recombinant antibody produced by a host cell. In a preferred embodiment, the antibody is a rabbit antibody.

In additional aspects, a host cell line is provided that expresses an antibody having specific binding for $\Delta^9$-THC and its metabolites, wherein said antibody comprises CDR amino acid sequences selected from the group consisting of L1: QASQSVYNNNQLS (SEQ ID NO:1); L2: GTSNLAS (SEQ ID NO:2); L3: QGGYTSGDGIA (SEQ ID NO:3); H1: GFSLSNYVLA (SEQ ID NO:4); H2: TIVSGTTYYASW (SEQ ID NO:5); H3: GLPHYITGDI (SEQ ID NO:6) or homologous amino acid sequences having at least 85% homology thereto. The host cell can be any cell capable of expressing antibody. In a preferred embodiment, the host cell is a HEK 293 cell.

In an additional aspect, an immunoassay for detecting the presence of THC and its metabolites in a sample is provided. Preferably the immunoassay utilizes an antibody having specific binding for THC and its metabolites, wherein said antibody comprises CDR amino acid sequences selected from the group consisting of L1: QASQSVYNNNQLS (SEQ ID NO:1); L2: GTSNLAS (SEQ ID NO:2); L3: QGGYTSGD-GIA (SEQ ID NO:3); H1: GFSLSNYVLA (SEQ ID NO:4); H2: TIVSGTTYYASW (SEQ ID NO:5); H3: GLPHYITGDI (SEQ ID NO:6) or homologous amino acid sequences having at least 85% homology thereto. In a preferred embodiment, the antibody is labeled or conjugated to a solid support such as microparticles or a solid surface. In a particularly preferred embodiment, the immunoassay is a lateral flow immunoassay strip for detecting the presence of THC and/or its metabolites in a fluid sample.

In yet another aspect, a method is provided for detecting the presence of THC in a sample, comprising the steps of: (1) providing a lateral flow immunoassay system comprising an antibody having specific binding for $\Delta^9$-THC; (2) contacting said lateral flow immunoassay system with a sample (e.g., an extract or sample of saliva obtained from an individual) to be tested for the presence of $\Delta^9$-THC in saliva; (3) performing the lateral flow immunoassay; (4) determining whether the immunoassay is positive or negative for the presence of $\Delta^9$-THC in the sample.

In an additional aspect, a kit is provided for testing for the presence of THC in saliva, comprising a lateral flow immunoassay strip for THC, and instructions for performing the test.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Before the present invention is described in detail, it is to be understood that unless otherwise indicated this invention is not limited to specific amino acid sequences, conjugation methods, materials and test systems, or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a particle" includes two or more particles; reference to "an antibody" includes two or more antibodies, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The term "specific binding" refers to a binding affinity of an antibody to THC or its metabolites and analogs of at least $10^6$ M$^{-1}$, more preferably between about $10^7$ and about $10^{11}$ M$^{-1}$, or typically between about $10^8$ and $10^{10}$ M$^{-1}$.

The term "THC" refers to tetrahydrocannabinols in general, and more particularly, to the parent molecule commonly found in marijuana, $\Delta^9$-THC.

The term "antibody" is used in its broadest sense and includes the antibody classes such as IgG (and its subclasses IgG$_1$, IgG$_2$, etc.), IgA, IgD, IgE, IgM, as well as Fab, Fab$_2$, Fv, diabodies, and other forms of antibody variants, constructs and fragments known in the art.

The present invention provides an isolated antibody having specific binding for the parent THC ($\Delta^9$-THC) and/or its major metabolites, which is a significant advance over the performance of other antibodies known in the art which are not sufficiently sensitive for the parent $\Delta^9$-THC. Exhaustive testing was performed on additional murine anti-THC antibodies using ELISA assays but none of the murine antibodies provided satisfactory performance or binding characteristics for $\Delta^9$-THC.

The antibodies described herein present a significant increase in sensitivity of immunoassays such as lateral flow immunoassays and ELISA for THC and allow the determination of the presence of $\Delta^9$-THC as well as its metabolites with higher sensitivity than previously possible. The superior performance characteristics are demonstrated in Example 4.

The present invention also provides a hybridoma cell clone producing the antibody as a monoclonal antibody, a recombinant antibody, further molecularly engineered recombinant antibodies and host cells producing the recombinant antibodies. The invention also provides methods of using the antibody in immunochemical applications and immunoassays, particularly lateral chain flow immunoassays, and methods for detecting THC in body fluids, particularly saliva, and kits for determining the presence of THC.

The invention is described in more detail below with respect to each of these embodiments.

II. Antibodies

The present invention provides high sensitivity anti-THC antibodies having antigen binding regions for detecting the presence of THC and its analogs in body fluids. Any antibody having the requisite sensitivity and binding affinity can be utilized. Preferred antibodies include rabbit monoclonal antibodies. Particularly preferred antibodies include CDR sequences as follows: L1: QASQSVYNNNQLS (SEQ ID NO:1); L2: GTSNLAS (SEQ ID NO:2); L3: QGGYTSGDGIA (SEQ ID NO:3); H1: GFSLSNYVLA (SEQ ID NO:4); H2: TIVSGTTYYASW (SEQ ID NO:5); H3: GLPHYITGDI (SEQ ID NO:6). In addition, preferred antibodies comprise the amino acid sequence for the light chain variable region: QVLTQTPSPVSAAVGGTVTINCQASQS-VYNNNQLSWYQQKPGQPPKLLIYGTSNLASG VPSR-FKGSGSGTQFTLTISSVQCDDAATYYC-QGGYTSGDGIAFGGGTEVVVK (SEQ ID NO:7), and the heavy chain variable region: QSVEESGGRLVTPGT-PLTLTCTVSGFSLSNYVLAWVRQAPGK-GLEWIGTIVSGTTYYAS WAKGRFTISKTSTTVHL-KITSPTTEDTATYFCVRGLPHYITGDIWGPGTLVTVSLG (SEQ ID NO:8), with the CDR sequences (SEQ ID NOS: 1-6) indicated by underlining.

Conservative amino acid substitutions of these sequences are also encompassed within the scope of the anti-THC antibodies. Conservative amino acid substitutions are well known to those of skill in the art, and are generally defined as amino acid replacements that preserve the structure and functional properties of proteins. For example, the PAM250 and Blosum 45 similarity matrices can be utilized to determine which amino acids are most likely to be acceptable substitutions to an existing sequence without causing loss of native structure and function of the protein.

PAM 250 Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| C | 12 | | | | | | | | | | | | | | | | | | | |
| G | -3 | 5 | | | | | | | | | | | | | | | | | | |
| P | -3 | -1 | 6 | | | | | | | | | | | | | | | | | |
| S | 0 | 1 | 1 | 1 | | | | | | | | | | | | | | | | |
| A | -2 | 1 | 1 | 1 | 2 | | | | | | | | | | | | | | | |
| T | -2 | 0 | 0 | 1 | 1 | 3 | | | | | | | | | | | | | | |
| D | -5 | 1 | -1 | 0 | 0 | 0 | 4 | | | | | | | | | | | | | |
| E | -5 | 0 | -1 | 0 | 0 | 0 | 3 | 4 | | | | | | | | | | | | |
| N | -4 | 0 | -1 | 1 | 0 | 0 | 2 | 1 | 2 | | | | | | | | | | | |
| Q | -5 | -1 | 0 | -1 | 0 | -1 | 2 | 2 | 1 | 4 | | | | | | | | | | |
| H | -3 | -2 | 0 | -1 | -1 | -1 | 1 | 1 | 2 | 3 | 6 | | | | | | | | | |
| K | -5 | -2 | -1 | 0 | -1 | 0 | 0 | 0 | 1 | 1 | 0 | 5 | | | | | | | | |
| R | -4 | -3 | 0 | 0 | -2 | -1 | -1 | -1 | 0 | 1 | 2 | 3 | 6 | | | | | | | |
| V | -2 | -1 | -1 | -1 | 0 | 0 | -2 | -2 | -2 | -2 | -2 | -2 | -2 | 4 | | | | | | |
| M | -5 | -3 | -2 | -2 | -1 | -1 | -3 | -2 | 0 | -1 | -2 | 0 | 0 | 2 | 6 | | | | | |
| I | -2 | -3 | -2 | -1 | -1 | 0 | -2 | -2 | -2 | -2 | -2 | -2 | -2 | 4 | 2 | 5 | | | | |
| L | -6 | -4 | -3 | -3 | -2 | -2 | -4 | -3 | -3 | -2 | -2 | -3 | -3 | 2 | 4 | 2 | 6 | | | |
| F | -4 | -5 | -5 | -3 | -4 | -3 | -6 | -5 | -4 | -5 | -2 | -5 | -4 | -1 | 0 | 1 | 2 | 9 | | |
| Y | 0 | -5 | -5 | -3 | -3 | -3 | -4 | -4 | -2 | -4 | 0 | -4 | -5 | -2 | -2 | -1 | -1 | 7 | 10 | |
| W | -8 | -7 | -6 | -2 | -6 | -5 | -7 | -7 | -4 | -5 | -3 | -3 | 2 | -6 | -4 | -5 | -2 | 0 | 0 | 17 |

The PAM 250 matrix above is arranged such that similar amino acids are close to each other, therefore regions along the diagonal of the matrix contain only positive scores. These regions provide an objective basis for defining conservative substitutions, i.e., amino acids that replace each other more frequently than would be expected from random replacements are shown on the diagonal. The variation in the diagonal terms of the matrix reflects both how often an amino acid is found in protein sequences and how often it is observed to be replaced by other amino acids. Thus rare amino acids which are replaced infrequently have the highest scores.

Blosum 45 Amino Acid Similarity Matrix

| | G | P | D | E | N | H | Q | K | R | S |
|---|---|---|---|---|---|---|---|---|---|---|
| G | 7 | | | | | | | | | |
| P | -2 | 9 | | | | | | | | |
| D | -1 | -1 | 7 | | | | | | | |
| E | -2 | 0 | 2 | 6 | | | | | | |
| N | 0 | -2 | 2 | 0 | 6 | | | | | |
| H | -2 | -2 | 0 | 0 | 1 | 10 | | | | |
| Q | -2 | -1 | 0 | 2 | 0 | 1 | 6 | | | |
| K | -2 | -1 | 0 | 1 | 0 | -1 | 1 | 5 | | |
| R | -2 | -2 | -1 | 0 | 0 | 0 | 1 | 3 | 7 | |
| S | 0 | -1 | 0 | 0 | 1 | -1 | 0 | -1 | -1 | 4 |

-continued

```
T  -2  -1  -1  -1   0  -2  -1  -1  -1   2   5
A   0  -1  -2  -1  -1  -2  -1  -1  -2   1   0   5
M  -2  -2  -3  -2  -2   0   0  -1  -1  -2  -1  -1   6
V  -3  -3  -3  -3  -3  -3  -2  -2  -1   0   0   1   5
I  -4  -2  -4  -3  -2  -3  -2  -3  -3  -2  -1  -1   2   3   5
L  -3  -3  -3  -2  -3  -2  -2  -3  -2  -3  -1  -1   2   1   2   5
F  -3  -3  -4  -3  -2  -2  -4  -3  -2  -2  -1  -2   0   0   0   1   8
Y  -3  -3  -2  -2  -2   2  -1  -1  -1  -2  -1  -2   0  -1   0   0   3   8
W  -2  -3  -4  -3  -4  -3  -2  -2  -2  -4  -3  -2  -2  -3  -2  -2   1   3  15
C  -3  -4  -3  -3  -2  -3  -3  -3  -3  -1  -1  -1  -2  -1  -3  -2  -2  -3  -5  12
    G   P   D   E   N   H   Q   K   R   S   T   A   M   V   I   L   F   Y   W   C
```

For a discussion of widely used matrices (including both PAM and Blosum matrices), see the following references: generally: "Amino acid substitution matrices from an information theoretic perspective," Altschul, S. F. (1991) *Journal of Molecular Biology* 219, 555-665; PAM matrices for proteins: "A model of evolutionary change in proteins," Dayhoff, M. O., Schwartz, R. M., Orcutt, B. C. (1978) In "Atlas of Protein Sequence and Structure" 5(3) M. O. Dayhoff (ed.), pp. 345-352, National Biomedical Research Foundation, Washington; PAM matrices for nucleic acids: "Improved Sensitivity of Nucleic Acid Database Search Using Application-Specific Scoring Matrices," States, D. J., Gish, W., Altschul, S. F. (1991) *Methods: A companion to Methods in Enzymology* 3(1), 66-77; Blosum (Block sums) matrices: "Amino acid substitution matrices from protein blocks," Steven Henikoff and Jorja G. Henikoff, (1992) *Proc. Natl. Acad. Sci. USA* 89 (Biochemistry), 10915-10919; Comparison of Amino Acid substitution matrices with visual representation of the differences:

"A Structural Basis of Sequence Comparisons: An evaluation of scoring methodologies," (1993) M. S. Johnson and J. P. Overington, *Journal of Molecular Biology* 233, 716-738; and "Performance Evaluation of Amino Acid Substitution Matrices" (1993) Steven Henikoff and Jorja G. Henikoff, Proteins: *Structure, Function, and Genetics* 17, 49-61.

The present invention also includes amino acid sequences which are homologous to SEQ ID NOS: 1-6, and the fragments above. As used herein, "homologous amino acid sequence" is any polypeptide which is encoded, in whole or in part, by a nucleic acid sequence which hybridizes at 25° C. to 35° C. below critical melting temperature ($T_m$), to any portion of the nucleic acid sequence encoding SEQ ID NOS: 1-6, or specifically to the nucleic acid sequences encoding the six CDR amino acid sequences, as shown below:

CDR-L1: CAG GCC AGT CAA AGT GTT TAT AAT AAC AAC CAA TTA TCC (SEQ ID NO:9);

CDR-L2: GGT ACA TCC AAT CTG GCA TCT (SEQ ID NO:10);

CDR-L3: CAA GGC GGT TAT ACT AGT GGT GAT GGT ATT GCT (SEQ ID NO:11);

CDR-H1: GGA TTC TCC CTC AGT AAC TAT GTA TTG GCC (SEQ ID NO:12);

CDR-H2: ACC ATT GTT AGC GGT ACC ACA TAC TAC GCG AGT TGG (SEQ ID NO:13);

CDR-H3: GGT TTG CCT CAT TAT ATT ACT GGG GAC ATC (SEQ ID NO:14).

A homologous amino acid sequence can be one that differs from an amino acid sequence shown in SEQ ID NOS: 1-6 by one or more conservative amino acid substitutions. Homologous amino acid sequences include sequences that are identical or substantially identical to SEQ ID NOS: 1-6. By "amino acid sequence substantially identical" is meant a sequence that is at least 85%, preferably 90%, more preferably 95%, most preferably 97%-99% identical to an amino acid sequence of reference and that preferably differs from the sequence of reference by a majority of conservative amino acid substitutions. Conservative amino acid substitutions are substitutions among amino acids of the same class. These classes include, for example, amino acids having uncharged polar side chains, such as asparagines (N), glutamine (Q), serine (S), threonine (T), and tyrosine (Y); amino acids having basic side chains, such as lysine (K), arginine (R), and histidine (H); amino acids having acidic side chains, such as aspartic acid (D) and glutamic acid (E); and amino acids having nonpolar side chains, such as glycine (G), alanine (A), valine (V), leucine (L), isoleucine (I), praline (P), phenylalanine (F), methionine (M), tryptophan (W), and cysteine (C). Homology can be measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps can be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 50%, 55%, 60%, 65%, 70%, 75%, 80%, and even more preferably 85%, 87%, 90%, 93%, 96% and most preferably 99% identical to a nucleotide sequence encoding amino acid sequences SEQ ID NOS:1-6.

In designing antigen binding regions (i.e., complementarity determining regions), typically, conservative amino acid substitutions are made such that the structure, hydrophobicity, charge, etc. of a particular amino acid or amino acid sequence is unchanged or changed only minimally. The objective is to maintain antigen binding affinity, but allow for maturation or adjustment of the binding affinity to identify additional amino acid sequences that provide useful binding characteristics to a given antigen. Conservative amino acid substitutions thus involve replacing one or more amino acids at a time with amino acids of the same type, i.e., amino acids having charged (basic or acidic) or uncharged polar side chains, or nonpolar side chains, for example, substitution of an uncharged amino acid such as asparagine (N), with another uncharged amino acid such as glutamine (Q), serine (S), threonine (T), or tyrosine (Y; substitution of a basic amino acid such as lysine (K), with another basic amino acid such as arginine (R) or histidine (H); substitution of an acidic amino acid such as aspartic acid (D), with another acidic amino acid such as glutamic acid (E); or substitution of a nonpolar amino acid such as glycine (G) with another nonpolar amino acid such as alanine (A), valine (V), leucine (L), isoleucine (I), methionine (M), proline (P), phenylalanine (F), tryptophan (W), or cysteine (C). Thus, conservative amino acid sequence substitutions are within the scope of the appended claims, so long as the overall sequence remains at least 85% homologous to each of SEQ ID NOS: 1-6. For example, such substitutions give rise to additional preferred CDR sequences, such as the following variations in L1, L2, L3, H1, H2, and H3:

L1: QATQSVYNNNQLS (SEQ ID NO:15), QASQSVYNNNQLT (SEQ ID NO:16), QASQTVYNNNQLS (SEQ ID NO:17), QASQSAYNNNQLS (SEQ ID NO:18), QVSQSVYNNNQLS (SEQ ID NO:19), QASQSVYNNNQIS (SEQ ID NO:20), QASQSVFNNNQLS (SEQ ID NO:21), QASQSVYNNNQLS (SEQ ID NO:22), and the like;

L2: GTSNLAS (SEQ ID NO:23), GSSNLAS (SEQ ID NO:24), GTSNLAT (SEQ ID NO:25), GTSNIAS (SEQ ID NO:26), GTSNLVS (SEQ ID NO:27), GTSNLAS (SEQ ID NO:28), GSSNIAS (SEQ ID NO:29), GTTNLVS (SEQ ID NO:30), and the like;

L3: QGGYTSGDGIA (SEQ ID NO:31); QGAYTSGDGIA (SEQ ID NO:32); QGGYSSGDGIA (SEQ ID NO:33); QGGYTSGEGIA (SEQ ID NO:34); QGGYTSGDGLA (SEQ ID NO:35); QGGYTSGDGIV (SEQ ID NO:36); QGGFTSGDGIA (SEQ ID NO:37); QGGYTTGEGIA (SEQ ID NO:38), and the like;

H1: GFSLSNYVLA (SEQ ID NO:39), GYSLSNYVLA (SEQ ID NO:40), GFTLSNYVLA (SEQ ID NO:41), GFSLTNYVLA (SEQ ID NO:42), GFSLSNFVLA (SEQ ID NO:43), GFSLSNYVIA (SEQ ID NO:44), GFSLSNYVLV (SEQ ID NO:45), and the like;

H2: TIVSGTTYYASW (SEQ ID NO:46), TLVSGTTYYASW (SEQ ID NO:47), TIVSGTSYYASW (SEQ ID NO:48), TIVSGTTYYVSW (SEQ ID NO:49), TIVSGTTFYASW (SEQ ID NO:50), TIVSGSTYYATW (SEQ ID NO:51), and the like;

H3: GLPHFITGDI (SEQ ID NO:52), GIPHYITGDI (SEQ ID NO:53), GLPHYITGDL (SEQ ID NO:54), GLPHYLTGDI (SEQ ID NO:55), GLPHYITGEI (SEQ ID NO:56), GLPNYITGDI (SEQ ID NO:57), GLPHFITGEI (SEQ ID NO:58), and the like.

These and other conservative amino acid substitutions are contemplated, as well as combinations thereof. In general such substitutions include no more than about 5% changes from the preferred sequences, preferably no more than about 10% changes and most preferably, no more than about 15% changes in the preferred sequences. Such sequences are 95%, 90% and 85% homologous, respectively, with the preferred CDR sequences.

In addition, each CDR sequence can be substituted independently, such that one CDR sequence can remain unsubstituted while one or more of the other CDR sequences can have one or more amino acid substitutions, as desired. One skilled in the art can easily envision acceptable substitutions and using recombinant methodologies, prepare and test the resulting antibody variants for binding to THC. In this manner, variants and improvements on the preferred CDR sequences disclosed above can be prepared, enabling the practice of the full scope of the invention.

In an additional embodiment, there is provided an antibody that specifically binds to THC and has CDR1 in the $V_L$ region ($V_L$/CDR1) comprising the amino acid sequence of Q $X_1$ $X_2$ Q $X_3$ $X_4$ $X_5$ N N N Q $X_6$ $X_7$ (SEQ ID NO:59) wherein $X_1$ can be G, A or V; $X_2$ is S or T; $X_3$ is S or T; $X_4$ is M, L, I, or V; $X_5$ is Y, or F; $X_6$ is L, I; $X_7$ is S or T.

In an additional embodiment, there is provided an antibody that specifically binds to THC and has CDR2 in the $V_L$ region ($V_L$/CDR2) comprising the amino acid sequence of G $X_1$ $X_2$ $X_3$ $X_4$ $X_5$ $X_6$ (SEQ ID NO:60), wherein $X_1$, $X_2$, $X_3$ and $X_6$ can be T, Y, S, Q or N; and $X_4$ and $X_5$ can be G, A, V, L, I, M, P, F, W or C.

In an additional embodiment, there is provided an antibody that specifically binds to THC and has CDR3 in the $V_L$ region ($V_L$/CDR3) comprising the amino acid sequence of Q $X_1$ $X_2$ $X_3$ $X_4$ $X_5$ $X_6$ $X_7$ $X_8$ $X_9$ $X_{10}$, (SEQ ID NO:61), wherein $X_1$, $X_2$, $X_6$ and $X_8$, $X_9$ and $X_{10}$ can be G, A, V, L, I, M, P, F, W or C; $X_3$, $X_4$ and $X_5$ can be T, Y, S, Q or N; $X_7$ can be D or E.

In an additional embodiment, there is provided an antibody that specifically binds to THC and has CDR1 in the $V_H$ region ($V_H$/CDR1) comprising the amino acid sequence of $X_1$ $X_2$ $X_3$ $X_4$ $X_5$ $X_6$ $X_7$ $X_8$ $X_9$ $X_{10}$, (SEQ ID NO:62), wherein $X_1$, $X_4$, $X_8$, $X_9$ and $X_{10}$ can be G, A, V, L, M or I; $X_2$ and $X_7$ can be F, W or Y; $X_3$, and $X_5$ can be T, Y, or S; and $X_6$ can be N or Q.

In an additional embodiment, there is provided an antibody that specifically binds to THC and has CDR2 in the $V_H$ region ($V_H$/CDR2) comprising the amino acid sequence of $X_1$ $X_2$ $X_3$ $X_4$ $X_5$ $X_6$ $X_7$ $X_8$ $X_9$ $X_{10}$ $X_{11}$ $X_{12}$, (SEQ ID NO:63), wherein $X_1$, $X_4$, $X_6$, $X_7$ and $X_{11}$ can be T, S or Y; $X_2$, $X_3$ or $X_{10}$, can be G, A, V, L, M or I; $X_5$ can be G, V, A, L or I, $X_8$ and $X_9$ can be F or Y, and $X_{12}$ can be W, Y or F.

In an additional embodiment, there is provided an antibody that specifically binds to THC and has CDR3 in the $V_H$ region ($V_H$/CDR3) comprising the amino acid sequence of $X_1$ $X_2$ P $X_3$ $X_4$ $X_5$ $X_6$ $X_7$ $X_8$ $X_9$, (SEQ ID NO:64), wherein $X_1$, $X_2$, $X_5$ $X_7$ and $X_9$ can be G, L, M, I, V, or A, $X_6$ can be T, S or Y, $X_8$ can be D or E, $X_3$ can be H, K or R, $X_4$ can be Y or F.

The anti-THC antibodies may be synthesized or expressed in cells of any organism, including but not limited to bacteria, yeast, plant, insect, and mammal. Particular types of cells include, but are not limited to, *Drosophila melanogaster* cells, *Saccharomyces cerevisiae* and other yeasts, *E. coli, Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. Examples of mammalian cells include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes.

The anti-THC antibodies can be purified or isolated after expression according to methods known to those skilled in the art. Examples of purification methods include electrophoretic, molecular, immunological and chromatographic techniques, including ion exchange, hydrophobic, affinity, and reverse-phase HPLC chromatography, and chromatofocusing, and the like. The degree of purification necessary will vary depending on the contaminants present with the antibodies. In some instances no purification will be necessary.

Also according to any of the embodiments described above, the anti-THC antibodies can be screened for a desired function, preferably a biological function such as their binding to THC or particular metabolites or analogs thereof. Screening assays are well known to those skilled in the art of immunoassays and immunochemistry, and include without limitation, ELISAs, flow cytometry, immunodiffusion precipitation assays, and the like.

The anti-THC antibodies can be used as affinity purification agents. In this process, the antibodies are immobilized on a solid phase such a Sephadex resin or filter paper, using methods well known in the art. The immobilized antibody is contacted with a sample containing THC or metabolites or analogs thereof, and thereafter the support is washed with a suitable solvent that will remove substantially all the material in the sample except the THC, which is bound to the immobilized antibody. Finally, the support is washed with another suitable solvent, such as glycine buffer, pH 5.0, that will release the THC from the antibody.

Anti-THC antibodies can also be useful in diagnostic assays for THC or its metabolites, e.g., detecting its presence in specific cells, tissues, or body fluids, such as saliva, serum or urine. Such diagnostic methods are useful in detecting and managing THC abuse, or dosing, such as when performing pharmacokinetic studies.

For diagnostic applications, the THC binding antibody can be labeled with a detectable moiety. For example, the antibody can be labeled with a radioisotope, such as $^{35}$S, $^{14}$C, $^{125}$I, $^{3}$H, and $^{131}$I, and the like, using techniques such as those described in Current Protocols in Immunology, Volumes 1 and 2, Coligen et al., Ed., Wiley-Interscience, New York, N.Y., Pubs. (1991). for example. Radioactive labeling can be measured using scintillation counting, for example.

The THC binding antibody can also be conjugated with a fluorescent label such as, without limitation, rare earth chelates (e.g., europium chelates), fluorescein and its derivatives, rhodamine and its derivatives, dansyl, Lissamine, phycoerythrin and Texas Red. The fluorescent labels can be conjugated to the antibody using techniques disclosed in Current Protocols in Immunology, supra, for example. Fluorescence can be quantified using a fluorimeter or UV/vis spectrophotometer using the known extinction coefficient of the fluorescent label.

The THC binding antibody can be labeled with various enzyme-substrate labels such as those disclosed in U.S. Pat. No. 4,275,149. The enzyme generally catalyzes a chemical alteration of a chromogenic substrate which can be measured using various techniques, typically optical absorption. For example, the enzyme may catalyze a color change in a substrate, which can be measured spectrophotometrically. Alternatively, the enzyme may alter the fluorescence or chemiluminescence of the substrate. The labeled anti-THC antibodies can be used for immunohistochemistry as well.

The THC binding antibody can be labeled with various particles such as that are not limited to any particular materials, and can comprise metals such as colloidal gold, natural polymers such as latex (e.g., latex particle, latex microparticle), polymer microspheres or microbeads, quantum dots, magnetic particles, glass beads, and the like. Preferably, the particles are detectable and can be easily visualized by eye or using an instrument, for example, by being colored.

Affinity maturation experiments can be performed in silico or in vitro, to optimize the CDR amino acid sequences to increase the binding affinity for THC or a specific metabolite or analog of THC. Affinity maturation techniques are known in the art and include the methods taught, for example, in U.S. Patent Application Publication Nos. 2004/0133357 and 2003/0022240. In addition to, or as an alternative to affinity maturation of the CDR sequences, the framework regions of the THC binding antibodies described herein can be subjected to mutagenesis and/or amino acid substitution, making conservative amino acid substitutions, or nonconservative amino acid substitutions, according to theoretical predictions based on protein structural databases, protein modeling and force field calculations, and the like. For example, energy scoring functions utilizing electrostatic interactions, van der Waals interactions, electrostatic solvation energy, solvent-accessible surface solvation energy, and conformational entropy can be incorporated into the affinity maturation methods. Force fields such as the Amber force field, Charmm force fields, the Discover cvff force fields, the ECEPP force fields, the GROMOS force fields, the OPLS force fields, the MMFF94 force field, the Tripos force field, the MM3 force field, the Dreiding force field, and UNRES force field, and other knowledge-based statistical force field (mean field) and structure-based thermodynamic potential functions can also be helpful in providing guidance for amino acid substitutions to optimize or provide selectivity between the parent $\Delta^9$-THC molecule and THC metabolites or analogs, etc.

III. Analytes

Analytes to be measured using the present immunoassays include $\Delta^9$-THC and its metabolites, analogs, precursors and derivatives, and the like, without limitation. Preferably, the anti-THC antibodies bind $\Delta^9$-THC with highest affinity and thereby provide a more sensitive assay for $\Delta^9$-THC, which can be present in unmetabolized form in body fluid (e.g, serum, saliva), in contrast to other THC assays which measure THC metabolites in urine or serum. In another preferred embodiment, the anti-THC antibodies bind $\Delta^9$-THC-COOH. Preferably, the anti-THC antibodies also bind to protein-conjugated THC or protein conjugated THC metabolites with high affinity.

IV. Obtaining Saliva Samples for Testing

There are several problems associated with obtaining samples for drug testing from subjects, including privacy issues associated with sample collection, maintenance of sample chain of custody, prevention of sample adulteration by the subject, and facilitating more rapid turn around time on sample analyses. Drug testing protocols utilizing urine samples present invasion of privacy issues. For example, with urine samples, it is necessary to observe the individual providing the sample to maintain the chain of custody and eliminate the possibility of sample switching or adulteration. Urine samples are also not a good indicator of the current level of intoxication since many drug metabolites continue to be excreted into urine for days or weeks after the drugs are initially taken. While blood samples do not suffer from these problems, collecting blood is an invasive procedure requiring special facilities and trained personnel that may not always be available when the need arises. It is necessary for law enforcement personnel to maintain strict chain of custody for all samples collected to ensure that mishandling or deliberate tampering do not occur. A break or even a perceived break in the chain of custody can result in evidence being dismissed outright or given little weight.

The assays utilizing the anti-THC antibodies described herein solve these problems in several ways. First, integration of the antibody into the drug test makes identification of the sample donor integral to the test and eliminates the need for complex chain of custody procedures. Second, a saliva-based drug test is better than a urine test for determining recent THC use because the non-metabolized drug, $\Delta^9$-THC, is the main form of THC present in the marijuana smoker's oral fluid sample. Thus the presence of $\Delta^9$-THC in oral fluids is an excellent indicator of recent marijuana consumption and may indicate that the person is under the drug's influence. In addition, drug levels in saliva can be readily correlated with drug levels in blood, therefore providing a better indicator of current drug use. Saliva samples from a subject can also be collected easily in view of a law enforcement officer without invasion of privacy and without using invasive methods. Finally, the present tests are easy to use and can be quickly performed by law enforcement or other personnel on site.

Accordingly, saliva samples can be conveniently collected and transferred to the testing device or assay using one of the embodiments of the devices disclosed for fluid collection and testing in U.S. Pat. No. 6,468,474 to Bachand, which discloses a saliva testing and confirmation device that generally includes an expresser cup adapted to receive and compress a foam collection swab pressed into the cup. The swab includes a sponge or foam portion capable of absorbing a fluid specimen such as saliva, and a generally rigid handle for facilitating manipulation thereof. The device also includes a testing and confirmation platform integral with the expresser cup. A channel or groove in the cup is provided for directing a flow of expressed fluid from the expresser into both a test well and a confirmation well. A lateral flow reagent test strip, in fluid communication with the test well may be encased in the platform and partially revealed for analysis of test results. The confirmation well includes a fluid tight cap having a tamper evident seal.

Additional fluid collection devices are disclosed in U.S. Ser. No. 10/942,493, published as U.S. Patent Application Publication No. 2006/0057027 by Hudak, et al. Briefly, the fluid collection and testing devices include a collection vial having a bottom and an open top along with an expresser sized for insertion into the vial open end. The expresser includes a ribbed base enabling fluid to pass therethrough and a support member holds the expresser within the collection vial with the ribbed base in a spaced apart relationship with the vial bottom. A fluid collector includes an absorbent member capturing a fluid and the absorbent member is sized for insertion into the expresser and is compressible against the ribbed base for releasing captured fluid through the ribbed base and into the vial bottom. A catch mechanism is provided for latching the fluid collector to the expresser after insertion into the expresser for enabling simultaneous removal of the expresser and the fluid collector from the collection vial.

V. Assays

The THC binding antibodies described herein can be used in any diagnostic or analytic assay to determine the presence of THC or its analogs, metabolites, etc. There are many types of immunoassays and immunochemical applications known in the art, including, but not limited to, ELISAs, western blotting, immunohistochemical assays, radioimmunoassays, fluorescence immunoassays, immunocytochemical assays, immunoaffinity chromatography, immunoprecipitation, flow cytometry, and the like. Any of these assay format and detection schemes can be performed using the anti-THC antibodies described herein. Preferred assays using the anti-THC antibodies of the invention include, without limitation, ELISAs, histoimmunochemical assays, lateral flow immunoassays, continuous flow displacement assays, and the like, as discussed further below. The assays can be used in competitive or noncompetitive manners and with any number of detection aids such as conjugating the anti-THC antibodies or THC or THC analogs to labels, enzymes, or particles, or the like, as will be readily understood by one skilled in the art.

A. General Considerations of Immunoassays

The most common type of immunoassay is competitive and non-competitive heterogeneous assays, such as enzyme-linked immunosorbent assays (ELISA). In a non-competitive ELISA, unlabeled antigen is bound to a solid support or reaction vessel, such as the surface of a microtiter plate or biochip. Biological sample is combined with antigens bound to the reaction vessel, and antibodies (primary antibodies) in the biological sample are allowed to bind to the antigens, thus forming the immune complexes. After the immune complexes have formed, excess biological sample is removed and the vessel is washed to remove nonspecifically bound antibodies. The immune complexes are then reacted with an appropriate enzyme-labeled anti-immunoglobulin (secondary antibody). The secondary antibody reacts with antibodies in the immune complexes, not with other antigens bound to the vessel. Secondary antibodies specific for binding antibodies of different species, including humans, are well known in the art and are commercially available, such as from Sigma Chemical Co. (St. Louis, Mo.) and Santa Cruz Biotechnology (Santa Cruz, Calif.). After a second wash step, the enzyme substrate is added. The enzyme linked to the secondary antibody catalyzes a reaction that converts the substrate into a detectable product. When excess antigen is present, the amount of product is directly proportional to the amount of primary antibodies present in the biological sample. Preferably, the product is fluorescent or luminescent, which can be measured using technology and equipment well known in the art. It is also possible to use reaction schemes that result in a colored product, which can be measured spectrophotometrically.

Sandwich or capture assays can also be used to identify and quantify immune complexes. Sandwich assays are a mirror image of non-competitive ELISAs in that antibodies are bound to the solid phase and antigen in the biological sample is measured. These assays are particularly useful in detecting antigens, having multiple epitopes, that are present at low concentrations. This technique requires excess antibody to be attached to a solid phase, such as the biochip. The bound antibody is then incubated with the biological samples, and the antigens in the sample are allowed to form immune complexes with the bound antibody. The immune complex is incubated with an enzyme-linked secondary antibody, which recognizes the same or a different epitope on the antigen as the primary antibody. Hence, enzyme activity is directly proportional to the amount of antigen in the biological sample. D. M. Kemeny & S. J. Challacombe, ELISA and Other Solid Phase Immunoassays (1988).

Typical enzymes that can be linked to secondary antibodies include horseradish peroxidase, glucose oxidase, glucose-6-phosphate dehydrogenase, alkaline phosphatase, .beta.-galactosidase, and urease. Secondary antigen-specific antibodies linked to various enzymes are commercially available from, for example, Sigma Chemical Co. and Amersham Life Sciences (Arlington Heights, Ill.).

Competitive ELISAs are similar to noncompetitive ELISAs except that enzyme linked antibodies compete with unlabeled antibodies in the biological sample for limited antigen binding sites. Briefly, a limited number of antigens are bound to the solid support. Biological sample and enzyme-labeled antibodies are added to the solid support. Antigen-specific antibodies in the biological sample compete with enzyme-labeled antibodies for the limited number of antigens bound to the solid support. After immune complexes have formed, nonspecifically bound antibodies are removed by washing, enzyme substrate is added, and the enzyme activity is measured. No secondary antibody is required. Because the assay is competitive, enzyme activity is inversely proportional to the amount of antibodies in the biological sample.

An alternative competitive ELISA can also be used. In this alternative embodiment, limited amounts of antibodies from the biological sample are bound to the surface of the solid support as described herein. Labeled and unlabeled antigens are then brought into contact with the solids support such that the labeled and unlabeled antigens compete with each other for binding to the antibodies on the surface of the solid support. After immune complexes have formed, nonspecifically bound antigens are removed by washing. The immune complexes are detected by incubation with an enzyme-linked secondary antibody, which recognizes the same or a different epitope on the antigen as the primary antibody, as described above. The activity of the enzyme is then assayed, which yields a signal that is inversely proportional to the amount of antigen present.

Homogeneous immunoassays can also be used when utilizing the anti-THC antibodies of the present invention. Homogeneous immunoassays may be preferred for detection of low molecular weight compounds, such as hormones, therapeutic drugs, and illegal drugs that cannot be analyzed by other methods, or compounds found in high concentration.

In homogeneous techniques, bound or unbound antigens are enzyme-linked. When antibodies in the biological sample bind to the enzyme-linked antigen, steric hindrances inhibit the enzyme activity. Free antigens (i.e., not enzyme-linked) compete with the enzyme-linked antigen for limited antibody binding sites. Thus, enzyme activity is directly proportional to the concentration of antigen in the biological sample. Enzymes useful in homogeneous immunoassays include lysozyme, neuraminidase, trypsin, papain, bromelain, glucose-6-phosphate dehydrogenase, and .beta.-galactosidase. T. Persoon, Immunochemical Assays in the Clinical Laboratory, 5 Clinical Laboratory Science 31 (1992). Enzyme-linked antigens are commercially available or can be linked using various chemicals well known in the art, including glutaraldehyde and maleimide derivatives.

Fluorescent immunoassays can also be used when utilizing the Anti-THC antibodies of the present invention. Fluorescent immunoassays are similar to ELISAs except the enzyme is substituted for fluorescent compounds called fluorophores or fluorochromes. These compounds have the ability to absorb energy from incident light and emit the energy as light of a longer wavelength and lower energy. Fluorescein and rhodamine, usually in the form of isothiocyanates that can be readily coupled to antigens and antibodies, are most commonly used in the art. D. P. Stites et al., Basic and Clinical Immunology (1994). Fluorescein absorbs light of 490 to 495 nm in wavelength and emits light at 520 nm in wavelength. Tetramethylrhodamine absorbs light of 550 nm in wavelength and emits light of 580 nm in wavelength. Illustrative fluorescence-based detection methods include ELF-97 alkaline phosphatase substrate (Molecular Probes Inc., Eugene, Oreg.); PBXL1 and PBXL-3 (phycobilisomes conjugated to streptavidin) (Martek Biosciences Corp., Columbia, Md.); FITC and Texas Red labeled goat anti-human IgG (Jackson ImmunoResearch Laboratories, Inc., West Grove, Pa.); and B-Phycoerythrin and R-Phycoerythrin conjugated to streptavidin (Molecular Probes Inc.). ELF-97 is a nonfluorescent chemical that is digested by alkaline phosphatase to form a fluorescent molecule. Because of turn over of the alkaline phosphatase, use of the ELF-97 substrate results in signal amplification. Fluorescent molecules attached to secondary antibodies do not exhibit this amplification.

Phycobiliproteins isolated from algae, porphyrins, and chlorophylls, which all fluoresce at about 600 nm, are also being used in the art. I. Hemmila, Fluoroimmunoassays and Immunofluorometric Assays, 31 Clin. Chem. 359 (1985); U.S. Pat. No. 4,542,104. Phycobiliproteins and derivatives thereof are commercially available under the names R-phycoerythrin (PE) and Quantum Red™ from, for example, Sigma Chemical Co. In addition, Cy-conjugated secondary antibodies and antigens are useful in immunoassays and are commercially available. Cy-3, for example, is maximally excited at 554 nm and emits light of between 568 and 574 nm. Cy-3 is more hydrophilic than other fluorophores and thus has less of a tendency to bind nonspecifically or aggregate. Cy-conjugated compounds are commercially available from Amersham Life Sciences.

Illustrative luminescence-based detection methods include CSPD and CDP star alkaline phosphatase substrates (Roche Molecular Biochemicals); and SuperSignal®. horseradish peroxidase substrate (Pierce Chemical Co., Rockford, Ill.). Chemiluminescence, electroluminescence, and electro-chemiluminescenc-e (ECL) detection methods are also attractive means for quantifying antigens and antibodies in a biological sample. Luminescent compounds have the ability to absorb energy, which is released in the form of visible light upon excitation. In chemiluminescence, the excitation source is a chemical reaction; in electroluminescence the excitation source is an electric field; and in ECL an electric field induces a luminescent chemical reaction. Molecules used with ECL detection methods generally comprise an organic ligand and a transition metal. The organic ligand forms a chelate with one or more transition metal atoms forming an organometallic complex. Various organometallic and transition metal-organic ligand complexes have been used as ECL labels for detecting and quantifying analytes in biological samples. Due to their thermal, chemical, and photochemical stability, their intense emissions and long emission lifetimes, ruthenium, osmium, rhenium, iridium, and rhodium transition metals are favored in the art. The types of organic ligands are numerous and include anthracene and polypyridyl molecules and heterocyclic organic compounds. For example, bipyridyl, bipyrazyl, terpyridyl, and phenanthrolyl, and derivatives thereof, are common organic ligands in the art. A common organometallic complex used in the art includes tris-bipyridine ruthenium (II), commercially available from IGEN, Inc. (Rockville, Md.) and Sigma Chemical Co.

Advantageously, ECL can be performed under aqueous conditions and under physiological pH, thus minimizing biological sample handling. J. K. Leland et al., Electrogenerated Chemiluminescence: An Oxidative-Reduction Type ECL Reactions Sequence Using Triprophyl Amine, 137 J. Electrochemical Soc. 3127-3131 (1990); WO 90/05296; U.S. Pat. No. 5,541,113. Moreover, the luminescence of these compounds may be enhanced by the addition of various cofactors, such as amines.

In practice, a tris-bipyridine ruthenium (II) complex, for example, may be attached to a secondary antibody using strategies well known in the art, including attachment to lysine amino groups, cysteine suithydryl groups, and histidine imidazole groups. In a typical ELISA immunoassay, secondary antibodies would recognize ISAs bound to antigens, but not unbound antigens. After washing nonspecific binding complexes, the tris-bipyridine ruthenium (II) complex would be excited by chemical, photochemical, and electrochemical excitation means, such as by applying current to the biochip. E.g., WO 86/02734. The excitation would result in a double oxidation reaction of the tris-bipyridine ruthenium (II) complex, resulting in luminescence that could be detected by, for example, a photomultiplier tube. Instruments for detecting luminescence are well known in the art and are commercially available, for example, from IGEN, Inc. Solid state color detection circuitry can also be used to monitor the color reactions on the biochip and, on command, compare the color patterns before and after the sample application. A color camera image can also be used and the pixel information analyzed to obtain the same information.

Still another detection method involves detection using a surface plasmon resonance (SPR) chip. The surface of the chip is scanned before and after sample application and a comparison is made. The SPR chip relies on the refraction of light when the molecules of interest are exposed to a light source. Each molecule has its own refraction index by which it can be identified. This method requires precise positioning and control circuitry to scan the chip accurately.

Yet another method involves a fluid rinse of the biochip with a fluorescing reagent. The locations that combine with the biological sample will fluoresce and can be detected with a charge-coupled device (CCD) array. The output of such a CCD array is analyzed to determine the unique pattern associated with each sample. This approach avoids the problems associated with scanning technologies. Speed is not a factor with any of the methods since the chemical combining of sample and reference takes only a few minutes to occur.

Moreover, array scanners are commercially available, such as from Genetic MicroSystems. The GMS 418 Array Scanner uses laser optics to rapidly move a focused beam of light over the biochip. This system uses a dual-wavelength system including high-powered, solid-state lasers that generate high excitation energy to allow for reduced excitation time. At a scanning speed of 30 Hz, the GMS 418 can scan a 22.times.75-mm slide with 10-.mu.m resolution in about 4 minutes.

Software for image analysis obtained with an array scanner is readily available. Available software packages include Ima-Gene (BioDiscovery, Los Angeles, Calif.); ScanAlyze (available at no charge; developed by Mike Eisen, Stanford University); DeArray (developed by Yidong Chen and Jeff Trent of the National Institutes of Health; used with IP Lab from Scanalytics, Fairfax, Va.); Pathways (Research Genetics, Huntsville, Ala.); GEM tools (Incyte Pharmaceuticals, Inc., Palo Alto, Calif.); and Imaging Research (Amersham Pharmacia Biotech, Inc., Piscataway, N.J.).

B. Lateral Flow Immunoassays

In a preferred embodiment, the THC binding antibody is utilized in a lateral flow immunoassay. Lateral Flow immunoassays are described, for example, in U.S. Pat. Nos. 5,770,458 to Klimov, 6,001,658 to Fredrickson and 6,368,876 to Huang. Lateral flow immunoassay is based on the principle of competitive binding. Analytes (e.g., drugs, THC) that may be present in the aqueous sample to be tested (e.g., an oral fluid specimen) compete against their respective conjugate for binding sites on an antibody having specific binding activity for the drug that is conjugated to a visible (e.g., colored) particle. The particles that can be used are not limited to any particular materials, and can comprise metals such as colloidal gold, natural polymers such as latex (e.g., latex particle, latex microparticle), polymer microspheres or microbeads, quantum dots, magnetic particles, glass beads, and the like. During testing, a portion of the oral fluid specimen migrates upward by capillary action. A drug, if present in the oral fluid specimen below its cut-off concentration, will not saturate the binding sites of an antibody having specific binding activity for the drug. The antibody without bound antigen will then react with the drug-protein conjugate, and a visible colored line will show up in the test line region of the specific drug strip due to the colored particle conjugated to the antibody. However, in the presence of drug above the cut-off concentration in the oral fluid specimen, the binding sites of the antibody will be saturated and the antibody will not complex with the drug conjugate and form a visible line in the test line region. A drug-positive oral fluid specimen will not generate a colored line in the specific test line region of the strip because of drug competition, while a drug-negative oral fluid specimen will generate a line in the test line region because of the absence of drug competition. To serve as a procedural control, a colored line will always appear at the control line region, indicating that proper volume of specimen has been added and membrane wicking has occurred.

The lateral immunoassay test typically contains membrane strips coated with drug-protein conjugates (purified bovine albumin) on the test line, an anti-antibody (e.g., a goat polyclonal anti-rabbit or anti-mouse antibody) or anti-BSA antibody against gold-protein conjugate at the control line, and a dye pad which contains particles, such as colloidal gold particles, coated with a monoclonal antibody specific to the drug to be tested (e.g., $\Delta^9$-THC or its metabolites).

In a particularly preferred embodiment, the anti-THC antibody is a recombinant rabbit antibody comprising CDR amino acid sequences selected from L1: QASQSVYNNNQLS (SEQ ID NO:1); L2: GTSNLAS (SEQ ID NO:2); L3: QGGYTSGDGIA (SEQ ID NO:3); H1: GFSLSNYVLA (SEQ ID NO:4); H2: TIVSGTTYYASW (SEQ ID NO:5); H3: GLPHYITGDI (SEQ ID NO:6) and homologous amino acid sequences having at least 85% homology thereto. A lateral flow immunoassay utilizing this antibody provides a much greater sensitivity and specificity for $\Delta^9$-THC than provided by murine anti-THC antibodies tested, as described in Example 4, and is particularly suitable and useful for oral fluid testing for the presence of $\Delta^9$-THC.

In an additional preferred embodiment, the anti-THC antibody comprises the amino acid sequence for the light chain variable region: QVLTQTPSPVSAAVGGTVTINCQASQSVYNNNQLSWYQQKPGQPPKLLIYGTSNLASG VPSRFKGSGSGTQFTLTISSVQCDDAATYYC-QGGYTSGDGIAFGGGTEVVVK (SEQ ID NO:7), or homologous amino acid sequences having at least 85% homology thereto. In certain embodiments, the amino acid sequence has about 90% or 95%, or even greater homology thereto. In additional preferred embodiments, the anti-THC antibody comprises the amino acid sequence for the heavy chain variable region: QSVEESGGRLVTPGTPLTLTCTVSGFSLSNYVLAWVRQAPGKGLEWIGTIVSGTTYYAS WAKGRFTISKTSTTVHLKITSPTTED-TATYFCVRGLPHYITGDIWGPGTLVTVSLG (SEQ ID NO:8), or homologous amino acid sequences having at least 85% homology thereto. In certain embodiments, the amino acid sequence has about 90% or 95%, or even greater homology thereto. These sequences depict both the framework region sequences and the CDR sequences (indicated with underlining).

C. Continuous Flow Displacement Cannabinoid Immunoassay

The anti-THC antibodies described herein can also be used in a continuous flow displacement immunoassay for $\Delta^9$-THC or its metabolites. In a continuous flow displacement immunoassay for cannabinoids, the binding kinetics of the cannabinoid analyte (e.g., $\Delta^9$-THC or its metabolites) to the antibody play a very important role. To allow for determination of the presence of the cannabinoid analyte, a labeled tracer compound is allowed to compete with the cannabinoid analyte for binding to the antibody. Preferably, the binding kinetics of the antibody to the tracer compound provide a fast dissociation rate of the bound tracer from the antibody, thereby permitting a rapid binding of the cannabinoid analyte. In general, a continuous flow displacement cannabinoid immunoassay utilizes an antibody having a high affinity for the cannabinoid analyte and a lower affinity for the tracer. The affinity of the antibody for the tracer may be anywhere between 15-100% cross-reactivity. A preferred cannabinoid-based tracer has about 40-80% cross-reactivity for the antibody.

A typical continuous flow displacement cannabinoid immunoassay involves a solid-phase immobilized antibody to $\Delta^9$-THC or its metabolites. The antigen binding site of the antibody can be exposed to a synthetic labeled tracer to form a labeled synthetic tracer-antibody complex such that the antigen binding sites of the antibody are saturated with the labeled synthetic tracers. When a biological sample suspected of containing the analyte $\Delta^9$-THC is continuously flowed past the solid-phase immobilized antibody-labeled synthetic tracer complex, if $\Delta^9$-THC is present in the sample, the cannabinoid analyte binds to the antibody and displaces the labeled synthetic tracer. Detection of the labeled tracer downstream from the binding point indicates the presence and/or quantity of the analyte present in the biological sample. See U.S. Pat. No. 5,183,740 to Ligler, which is incorporated by reference herein.

The success of developing a continuous flow displacement immunoassay is based on the selection of antibody and tracer to achieve a fast dissociation rate of the bound tracer from the antibody, thereby permitting a rapid binding of the analyte. In general, the ideal continuous flow displacement immunoassay utilizes a system where the antibody has a high affinity for the analyte, and a lower affinity for the tracer. The affinity of the antibody for the tracer may be anywhere between 15-100% cross-reactivity. A preferred THC-based tracer has about 40-80% cross-reactivity for the antibody. In addition, the condition for displacing a tracer from the recognition molecule is preferably carried out in non-equilibrium condition or kinetic flow reaction, such that the sample flows past the recognition molecule-tracer complex at a rate where a stable equilibrium state between the recognition molecule, tracer, and analyte has not been achieved.

D. Additional Assay Formats

The anti-THC antibodies described herein can also be utilized in additional useful commercially marketed immunoassay formats, for example, the OnTrak TesTcup, On•Site Cup-Kit™, On•Site OraLab®, OnTrak TesTstik assay systems marketed by Varian, Inc.

VI. Pharmaceutical Applications and Formulations

The anti-THC antibodies described herein can also be utilized in pharmaceutical and therapeutic applications, for example, to treat overdose of THC or reduce serum concentrations of THC. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENT™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an antipsychotic agent. Such molecules are suitably present in combination in amounts that are effective for the purpose intended.

The active ingredients can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes. Therapeutic formulations of the antibodies can be prepared for storage by mixing the antibodies having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions.

Sustained-release preparations comprising the antibodies can be prepared. Suitable examples of sustained-release preparations include semipermeable matrices of solid hydrophobic polymers containing the antibodies, which matrices are in the form of shaped articles, e.g., films, or microcapsule. Examples of sustained-release matrices include polyesters, hydrogels (for example, poly(2-hydroxyethyl-1S methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For use in humans, humanization of the rabbit anti-THC antibody is required, and can be accomplished using methods such as those described in U.S. Pat. Nos. 6,800,738 to Carter, and 6,719,971. CDR repair can be effected if binding affinity and/or specificity is compromised utilizing, for example, the methods described in U.S. Patent Application Publication No. 20060122377, all of which are incorporated by reference herein in their entireties.

The antibodies can be administered to the patient by a variety of different means and will vary depending upon the intended application. As one skilled in the art would recognize, administration of the therapeutic compositions can be carried out in various fashions, and more typically by parenteral injection into body cavity or vessel, e.g., intraperitoneal, intravenous, intralymphatic, intratumoral, intramuscular, interstitial, intraarterial, subcutaneous, intralesional, intraocular, intrasynovial, intraarticular. However, other methods of administration can be utilized for particular purposes, for example, via topical administration, including, but not limited to, dermal, ocular and rectal; transdermal, via passive or active means, e.g., using a patch, a carrier, or iontophoresis; transmucosal, e.g., sublingual, buccal, rectal, vaginal, or transurethral; oral, e.g., gastric or duodenal; via inhalation, e.g., pulmonary or nasal inhalation, using e.g., a nebulizer.

Depending on the THC concentration in serum or other body fluids, about 1 µg/kg to about 50 mg/kg (e.g., 0.1-20 mg/kg, 0.5-15 mg/Kg, and 1-10 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until the THC levels have been reduced to a desired level. However, other dosage regimens may be useful. The progress of this therapy is easily monitored by conventional techniques and assays, including, for example, immunoassays of THC and/or its metabolites in urine or saliva.

It is to be understood that while the invention has been described in conjunction with the preferred specific embodiments thereof, that the description above as well as the examples that follow are intended to illustrate and not limit the scope of the invention. The practice of the present invention will employ, unless otherwise indicated, conventional techniques of immunochemistry, organic chemistry, polymer chemistry, biochemistry and the like, which are within the skill of the art. Other aspects, advantages and modifications within the scope of the invention will be apparent to those skilled in the art to which the invention pertains. Such techniques are explained fully in the literature.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric.

Example 1

Preparation of a Rabbit Monoclonal Antibody Having Specific Binding for THC

An antibody having specific binding for THC was prepared by the following procedures:

Immunization

New Zealand White rabbits were immunized. Rabbits were injected subcutaneously with 0.4 mg of THC-KLH in complete Freund's adjuvant. After the initial immunization, animals were boosted 5 more times every 21 days in the same manner with incomplete Freund's adjuvant and the sera tested by immunoassay and immunohistochemical staining. The rabbit with the best titer in the immunoassay and IHC (immunohistochemistry) was selected for a final intravenous boost of 0.4 mg of THC-KLH in saline, four days before removal of the spleen.

Hybridization, Fusion

Fusions were performed using conventional methodology: $1.5-3\times10^8$ lymphocytes from an immunized rabbit and the fusion partner (240E-w) were fused at a ratio of 2:1 with PEG 4000 at 37° C. in serum-free medium. The cells were distributed in 96-well cell culture plates at approximately $1\times10^5$ lymphocytes per well in medium with 15% FBS (or FCS), and after 48 hr HAT medium was added. Medium was changed 2-3 times before screening. Hybridoma colonies were ready for screening in 3-5 weeks. Supernatants were tested for the presence of antibody, specific for the immunogen, by ELISA. Immunohistochemistry was used as a secondary screening assay. The hybridomas were subcloned by limit dilution. For feeder cells, the fusion partner 240E-w at $2\times10^4$ cells per well was used.

ELISA

ELISA was performed in 96-well micro-titer plates that had been coated overnight with immunogen at 1.0 µg/ml, plates were then saturated with 2% BSA, followed by incubation with the antibody-containing supernatant for 1 hr at room temperature. After washing with PBS-Tween, alkaline phosphatase conjugated goat anti-rabbit immunoglobulin (IgG) was added and incubation continued for another hour; plates were washed again and developed in the presence of P-NPP (para-nitrophenyl phosphate). Color was read at 405 nm with a plate reader (Multiskan MCC/340 from Fisher Scientific).

Antibody Purification

Tissue culture supernatants containing rabbit monoclonal antibody against ER were incubated with Protein A immobilized on a column. The column was washed extensively with PBS to remove nonspecific binding proteins until the OD 280 was less than 0.01. The rabbit IgGs were eluted with 0.2 M, pH 2.5 citrate. The eluates was dialyzed against PBS overnight at 4° C. (28).

Antibody Affinity Assay

ELISA was performed to determine antibody affinities. 96-well micro-titer plates was coated overnight with the THC conjugated BSA or a human recombinant protein (1-300aa) at 1.0 ∝g/ml, respectively. The plates were saturated with 2% BSA, followed by incubation with the antibody serially diluted (200 nM, 100 nM, 50 nM, 25 nM, 12.5 nM, 6.25 nM, 3.125 nM, 1.56 nM, 0.78 nM, 0.39 nM, and 0.2 nM). ER clone SP1 was incubated with the wells coated with the BSA conjugated ER peptide and clone 1D5 was incubated with wells coated with ER alpha recombinant protein. Samples were in duplicate. After washing with PBS-Tween, HRP-conjugated goat anti-rabbit and mouse IgGs (Spring Bioscience Corporation, CA) were added. The plates were washed again, and were developed with TMB solution for 15 minutes. The reaction was stopped by adding 0.5N $H_2SO_4$. Optical density (OD) was measured at 450 nm.

Example 2 cDNA Cloning from Rabbit Hybridoma and Recombinant Antibody Expression mRNA was isolated from rabbit hybridomas by using Qiagen TurboCapture mRNA kit. cDNA was made directly in the TurboCapture tube by solid phase synthesis. Rabbit IgG cDNAs were amplified with heavy or light chain specific primers by PCR. For L chain, the PCR product was sequenced and a consensus sequence was found from three independent mRNA and PCR reactions. To make an expression construct, the PCR product was digested with restriction enzymes and cloned into an expression vector. A cDNA clone with the consensus PCR sequence was selected for expression. For H chain, only the variable region ($V_H$) was amplified and the PCR product was digested with the fusion partner $V_H$ specific restriction enzyme. Rabbit B-cell $V_H$ cDNA was purified and recovered from an agarose gel. In order to identify a desired cDNA clone, the purified $V_H$ product was cloned into pCR 2.1-TOPO vector (Invitrogen) and cDNA clones were screened. Then, the $V_H$ cDNA in the desired clone was subcloned into an expression vector with rabbit IgG heavy chain constant region (CH). To express recombinant antibody, both light and heavy chain expression constructs were transfected into HEK 293 by using 293fectin (Invitrogen) as a vehicle. Supernatant containing recombinant antibody transiently expressed from the cells were harvested after 5-day transfection.

The nucleotide and amino acid sequences for the THC binding antibody variable regions of the light chain ($V_L$) and the variable region of the heavy chain ($V_H$) are depicted below:

$V_L$ Nucleotide Sequence:

```
CAA GTG CTG ACC CAG ACT CCA TCC CCC GTG TCT GCA

GCT GTG GGA GGC ACA GTC ACC ATC AAT TGC CAG GCC

AGT CAA AGT GTT TAT AAT AAC AAC CAA TTA TCC TGG

TAT CAG CAG AAA CCA GGG CAG CCT CCC AAG CTC CTG

ATC TAT GGT ACA TCC AAT CTG GCA TCT GGG GTC CCA

TCG CGG TTC AAA GGC AGT GGA TCT GGG ACA CAG TTC

ACT CTC ACC ATC AGC AGC GTG CAG TGT GAC GAT GCT

GCC ACT TAC TAC TGT CAA GGC GGT TAT ACT AGT GGT

GAT GGT ATT GCT TTC GGC GGA GGG ACC GAG GTG GTC

GTC AAA (SEQ ID NO: 65)
```

$V_L$ Amino Acid Sequence:
QVLTQTPSPVSAAVGGTVTINCQASQS-VYNNNQLSWYQQKPGQPPKLLIYGTSNLASG VPSR-FKGSGSGTQFTLTISSVQCDDAATYYC-QGGYTSGDGIAFGGGTEVVVK (SEQ ID NO: 7)

$V_H$ Nucleotide Sequence:

```
CAG TCG GTG GAG GAG TCC GGG GGT CGC CTG GTC ACG

CCT GGG ACA CCC CTG ACA CTC ACC TGC ACA GTC TCT

GGA TTC TCC CTC AGT AAC TAT GTA TTG GCC TGG GTC

CGC CAG GCT CCA GGG AAG GGG CTG GAG TGG ATC GGA

ACC ATT GTT AGC GGT ACC ACA TAC TAC GCG AGT GGG

GCG AAA GGC CGA TTC ACC ATC TCC AAA ACC TCG ACC

ACG GTG CAT CTG AAA ATC ACC AGT CCG ACA ACC GAG

GAC ACG GCC ACC TAT TTC TGT GTC AGA GGT TTG CCT

CAT TAT ATT ACT GGG GAC ATC TGG GGC CCA GGC ACC

CTG GTC ACC GTC TCC TTA GGG (SEQ ID NO: 66)
```

$V_H$ Amino Acid Sequence:
QSVEESGGRLVTPGTPLTLTCTVSGFSL-SNYVLAWVRQAPGKGLEWIGTIVSGTTYYAS WAKGRFTISKTSTTVHLKITSPTTED-TATYFCVRGLPHYITGDIWGPGTLVTVSLG (SEQ ID NO: 8).

Example 3

Design of a Lateral Flow Immunoassay System Using a Rabbit Monoclonal Antibody for the Detection of THC in Saliva Antibodies to be utilized in lateral flow immunoassay systems were conjugated to particles that can be visualized. Conjugation conditions were tested for each antibody lot, and monobasic/dibasic phosphate buffer pH was adjusted to optimize the conjugation, which was typically between pH 6.5 and 8.5. Antibody was diluted to 0.1 mg/ml using monobasic/dibasic phosphate buffer at room temperature and mixed with gold particles (30 nm) in the proportion 20 µl antibody per 1 mL gold for 5 minutes. 10% BSA was added to create a 1:10 dilution BSA: total volume Gold solution, and mixing was continued for five (5) minutes. The sample was centrifuged at 10,000 rpm at 4° C. for forty (40) minutes, and the supernatant removed to achieve a final suspension at 10% (w/w) gold. The gold conjugated antibodies are then utilized in the lateral flow immunoassay system, such as the system sold under the tradename OraLab®.

Example 4

Comparison of a Lateral Flow Immunoassay System Using a Recombinant Rabbit Monoclonal Antibody with a Murine Monoclonal Antibody for the Detection of THC A murine monoclonal anti-THC antibody used in a lateral flow immunoassay was used as a comparator to assess the sensitivity of a recombinant rabbit anti-THC antibody in the same immunoassay system. The murine anti-THC antibody chosen for comparison exhibited a sensitivity higher or comparable to other available anti-THC antibodies used in lateral flow immunoassays.

To be directly comparable, both the mouse monoclonal anti-THC antibody and the recombinant rabbit anti-THC antibody were conjugated to gold particles using the same procedures. The conjugation buffer pH was adjusted to assure the best conjugation. All other materials and procedure were identical. Both a murine anti-THC antibody strip and a rabbit anti-THC antibody strip were prepared on the same card with the murine antibody strip on the left and rabbit antibody strip on the right.

Samples were prepared at the indicated parent THC concentrations. Two (2) mLs of each sample was placed in the collector, and squeezed into the tube. The cards were tested and read at 10 and 15 minutes respectively (n=3).

Results

Ten (10) Minute Color Reading

| | Parent THC Concentrations (ng/mL) | | | | | | | | | | | | | | | |
|---|---|---|---|---|---|---|---|---|---|---|---|---|---|---|---|---|
| | 0 | | | | 50 | | | | 100 | | | | 200 | | | |
| | | | | Ave. | | | | Ave. | | | | Ave. | | | | Ave. |
| Recombinant rabbit anti-THC | 2.2 | 2.5 | 1.8 | 2.17 | 0 | 0 | 0.2 | 0.07 | 0 | 0 | 0 | 0 | 0 | 0 | 0 | 0 |
| Mouse anti-THC | 2.2 | 2.2 | 2.0 | 2.13 | 1.2 | 1.7 | 1.0 | 1.30 | 1.0 | 1.5 | 1.0 | 1.17 | 0.7 | 1.2 | 0.5 | 0.8 |

Fifteen (15) Minute Color Reading

| | Parent THC Concentrations (ng/mL) | | | | | | | | | | | | | | | |
|---|---|---|---|---|---|---|---|---|---|---|---|---|---|---|---|---|
| | 0 | | | | 50 | | | | 100 | | | | 200 | | | |
| | | | | Ave. | | | | Ave. | | | | Ave. | | | | Ave. |
| Recombinant rabbit anti-THC | 2.5 | 2.7 | 2.3 | 2.50 | 0 | 0.2 | 0.2 | 0.13 | 0 | 0 | 0 | 0 | 0 | 0 | 0 | 0 |
| Mouse anti-THC | 2.5 | 2.4 | 2.5 | 2.47 | 1.5 | 2.2 | 2.0 | 1.90 | 1.2 | 2.0 | 1.5 | 1.57 | 0.7 | 1.5 | 0.5 | 0.9 |

Conclusion

The recombinant rabbit anti-THC antibody is more sensitive than the reference mouse anti-THC antibody. At 50 ng/mL THC, the reading with the murine anti-THC antibody is only slightly decreased, and only at THC concentrations of 200 ng/mL does the murine anti-THC antibody clearly indicate that THC was present in the sample solution tested. In contrast, the reading for the recombinant rabbit anti-THC antibody was almost completely abolished at a sample concentration of 50 ng/mL THC, indicating the presence of THC in the sample at the lowest concentration of THC tested. Using the recombinant rabbit anti-THC antibody in this test system, a sensitivity of 35 ng/mL or lower is achievable.

Example 5

Use of a Lateral Flow Immunoassay System for the Detection of THC

A lateral flow immunoassay system for the detection of THC is provided to an individual. The individual is instructed to open the collector bag, place the collector foam inside his or her mouth for three minutes, and completely saturate the collector foam with saliva. The individual or other user is instructed to place the OraLab® cassette (Varian, Inc. 25200 Commercentre Drive, Lake Forest, Calif.) on a flat surface and lift the confirmation well cap to assure unobstructed saliva flow into the well. The individual then removes the collector foam from his or her mouth, places it vertically into the sample well on top of the device, and pushes the collector downward while counting slowly to five until it stops. The user is instructed to push the cap down firmly to seal the confirmation well after ten minutes have passed, and to remove the label covering the results windows and interpret the results. When the saliva sample is negative for the presence of THC, the antibody-gold particles migrate with the fluid flow by capillary action until they reach the THC loaded line, where they stop and line up to indicate a negative result. When the saliva sample is positive for the presence of THC, the antibody-gold particles migrate with the fluid flow but do not stop at the THC loaded line and instead continue upwards to the positive zone, indicating a positive result.

---

SEQUENCE LISTING

```
<160> NUMBER OF SEQ ID NOS: 66

<210> SEQ ID NO 1
<211> LENGTH: 13
<212> TYPE: PRT
<213> ORGANISM: rabbit

<400> SEQUENCE: 1
```

```
Gln Ala Ser Gln Ser Val Tyr Asn Asn Gln Leu Ser
1               5                  10
```

<210> SEQ ID NO 2
<211> LENGTH: 7
<212> TYPE: PRT
<213> ORGANISM: rabbit

<400> SEQUENCE: 2

```
Gly Thr Ser Asn Leu Ala Ser
1               5
```

<210> SEQ ID NO 3
<211> LENGTH: 11
<212> TYPE: PRT
<213> ORGANISM: rabbit

<400> SEQUENCE: 3

```
Gln Gly Gly Tyr Thr Ser Gly Asp Gly Ile Ala
1               5                  10
```

<210> SEQ ID NO 4
<211> LENGTH: 10
<212> TYPE: PRT
<213> ORGANISM: rabbit

<400> SEQUENCE: 4

```
Gly Phe Ser Leu Ser Asn Tyr Val Leu Ala
1               5                  10
```

<210> SEQ ID NO 5
<211> LENGTH: 12
<212> TYPE: PRT
<213> ORGANISM: rabbit

<400> SEQUENCE: 5

```
Thr Ile Val Ser Gly Thr Thr Tyr Tyr Ala Ser Trp
1               5                  10
```

<210> SEQ ID NO 6
<211> LENGTH: 10
<212> TYPE: PRT
<213> ORGANISM: rabbit

<400> SEQUENCE: 6

```
Gly Leu Pro His Tyr Ile Thr Gly Asp Ile
1               5                  10
```

<210> SEQ ID NO 7
<211> LENGTH: 110
<212> TYPE: PRT
<213> ORGANISM: rabbit

<400> SEQUENCE: 7

```
Gln Val Leu Thr Gln Thr Pro Ser Pro Val Ser Ala Ala Val Gly Gly
1               5                  10                  15

Thr Val Thr Ile Asn Cys Gln Ala Ser Gln Ser Val Tyr Asn Asn Asn
                20                  25                  30

Gln Leu Ser Trp Tyr Gln Gln Lys Pro Gly Gln Pro Pro Lys Leu Leu
            35                  40                  45

Ile Tyr Gly Thr Ser Asn Leu Ala Ser Gly Val Pro Ser Arg Phe Lys
        50                  55                  60

Gly Ser Gly Ser Gly Thr Gln Phe Thr Leu Thr Ile Ser Ser Val Gln
```

-continued

```
                65                  70                  75                  80
        Cys Asp Asp Ala Ala Thr Tyr Tyr Cys Gln Gly Gly Tyr Thr Ser Gly
                        85                  90                  95

Asp Gly Ile Ala Phe Gly Gly Gly Thr Glu Val Val Val Lys
                        100                 105                 110

<210> SEQ ID NO 8
<211> LENGTH: 115
<212> TYPE: PRT
<213> ORGANISM: rabbit

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Val
                20                  25                  30

Leu Ala Trp Val Arg Gln Ala Pro Gly Lys Gly Leu Glu Trp Ile Gly
            35                  40                  45

Thr Ile Val Ser Gly Thr Thr Tyr Tyr Ala Ser Trp Ala Lys Gly Arg
        50                  55                  60

Phe Thr Ile Ser Lys Thr Ser Thr Thr Val His Leu Lys Ile Thr Ser
65                  70                  75                  80

Pro Thr Thr Glu Asp Thr Ala Thr Tyr Phe Cys Val Arg Gly Leu Pro
                85                  90                  95

His Tyr Ile Thr Gly Asp Ile Trp Gly Pro Gly Thr Leu Val Thr Val
                100                 105                 110

Ser Leu Gly
        115

<210> SEQ ID NO 9
<211> LENGTH: 39
<212> TYPE: DNA
<213> ORGANISM: rabbit

<400> SEQUENCE: 9
caggccagtc aaagtgttta taataacaac caattatcc                          39

<210> SEQ ID NO 10
<211> LENGTH: 21
<212> TYPE: DNA
<213> ORGANISM: rabbit

<400> SEQUENCE: 10
ggtacatcca atctggcatc t                                             21

<210> SEQ ID NO 11
<211> LENGTH: 33
<212> TYPE: DNA
<213> ORGANISM: rabbit

<400> SEQUENCE: 11
caaggcggtt atactagtgg tgatggtatt gct                                33

<210> SEQ ID NO 12
<211> LENGTH: 30
<212> TYPE: DNA
<213> ORGANISM: rabbit

<400> SEQUENCE: 12
ggattctccc tcagtaacta tgtattggcc                                    30
```

<210> SEQ ID NO 13
<211> LENGTH: 36
<212> TYPE: DNA
<213> ORGANISM: rabbit

<400> SEQUENCE: 13
accattgtta gcggtaccac atactacgcg agttgg                           36

<210> SEQ ID NO 14
<211> LENGTH: 30
<212> TYPE: DNA
<213> ORGANISM: rabbit

<400> SEQUENCE: 14
ggtttgcctc attatattac tggggacatc                                  30

<210> SEQ ID NO 15
<211> LENGTH: 13
<212> TYPE: PRT
<213> ORGANISM: artificial
<220> FEATURE:
<223> OTHER INFORMATION: chemically synthesized

<400> SEQUENCE: 15

Gln Ala Thr Gln Ser Val Tyr Asn Asn Asn Gln Leu Ser
1               5                   10

<210> SEQ ID NO 16
<211> LENGTH: 13
<212> TYPE: PRT
<213> ORGANISM: artificial
<220> FEATURE:
<223> OTHER INFORMATION: chemically synthesized

<400> SEQUENCE: 16

Gln Ala Ser Gln Ser Val Tyr Asn Asn Asn Gln Leu Thr
1               5                   10

<210> SEQ ID NO 17
<211> LENGTH: 13
<212> TYPE: PRT
<213> ORGANISM: artificial
<220> FEATURE:
<223> OTHER INFORMATION: chemically synthesized

<400> SEQUENCE: 17

Gln Ala Ser Gln Thr Val Tyr Asn Asn Asn Gln Leu Ser
1               5                   10

<210> SEQ ID NO 18
<211> LENGTH: 13
<212> TYPE: PRT
<213> ORGANISM: artificial
<220> FEATURE:
<223> OTHER INFORMATION: chemically synthesized

<400> SEQUENCE: 18

Gln Ala Ser Gln Ser Ala Tyr Asn Asn Asn Gln Leu Ser
1               5                   10

<210> SEQ ID NO 19
<211> LENGTH: 13
<212> TYPE: PRT
<213> ORGANISM: artificial
<220> FEATURE:

<223> OTHER INFORMATION: chemically synthesized

<400> SEQUENCE: 19

Gln Val Ser Gln Ser Val Tyr Asn Asn Asn Gln Leu Ser
1               5                   10

<210> SEQ ID NO 20
<211> LENGTH: 13
<212> TYPE: PRT
<213> ORGANISM: artificial
<220> FEATURE:
<223> OTHER INFORMATION: chemically synthesized

<400> SEQUENCE: 20

Gln Ala Ser Gln Ser Val Tyr Asn Asn Asn Gln Ile Ser
1               5                   10

<210> SEQ ID NO 21
<211> LENGTH: 13
<212> TYPE: PRT
<213> ORGANISM: artificial
<220> FEATURE:
<223> OTHER INFORMATION: chemically synthesized

<400> SEQUENCE: 21

Gln Ala Ser Gln Ser Val Phe Asn Asn Asn Gln Leu Ser
1               5                   10

<210> SEQ ID NO 22
<211> LENGTH: 13
<212> TYPE: PRT
<213> ORGANISM: artificial
<220> FEATURE:
<223> OTHER INFORMATION: chemically synthesized

<400> SEQUENCE: 22

Gln Ala Ser Gln Ser Val Tyr Asn Asn Asn Gln Leu Ser
1               5                   10

<210> SEQ ID NO 23
<211> LENGTH: 7
<212> TYPE: PRT
<213> ORGANISM: artificial
<220> FEATURE:
<223> OTHER INFORMATION: chemically synthesized

<400> SEQUENCE: 23

Gly Thr Ser Asn Leu Ala Ser
1               5

<210> SEQ ID NO 24
<211> LENGTH: 7
<212> TYPE: PRT
<213> ORGANISM: artificial
<220> FEATURE:
<223> OTHER INFORMATION: chemically synthesized

<400> SEQUENCE: 24

Gly Ser Ser Asn Leu Ala Ser
1               5

<210> SEQ ID NO 25
<211> LENGTH: 7
<212> TYPE: PRT
<213> ORGANISM: artificial
<220> FEATURE:
<223> OTHER INFORMATION: chemically synthesized

```
<400> SEQUENCE: 25

Gly Thr Ser Asn Leu Ala Thr
1               5

<210> SEQ ID NO 26
<211> LENGTH: 7
<212> TYPE: PRT
<213> ORGANISM: artificial
<220> FEATURE:
<223> OTHER INFORMATION: chemically synthesized

<400> SEQUENCE: 26

Gly Thr Ser Asn Ile Ala Ser
1               5

<210> SEQ ID NO 27
<211> LENGTH: 7
<212> TYPE: PRT
<213> ORGANISM: artificial
<220> FEATURE:
<223> OTHER INFORMATION: chemically synthesized

<400> SEQUENCE: 27

Gly Thr Ser Asn Leu Val Ser
1               5

<210> SEQ ID NO 28
<211> LENGTH: 7
<212> TYPE: PRT
<213> ORGANISM: artificial
<220> FEATURE:
<223> OTHER INFORMATION: chemically synthesized

<400> SEQUENCE: 28

Gly Thr Ser Asn Leu Ala Ser
1               5

<210> SEQ ID NO 29
<211> LENGTH: 7
<212> TYPE: PRT
<213> ORGANISM: artificial
<220> FEATURE:
<223> OTHER INFORMATION: chemically synthesized

<400> SEQUENCE: 29

Gly Ser Ser Asn Ile Ala Ser
1               5

<210> SEQ ID NO 30
<211> LENGTH: 7
<212> TYPE: PRT
<213> ORGANISM: artificial
<220> FEATURE:
<223> OTHER INFORMATION: chemically synthesized

<400> SEQUENCE: 30

Gly Thr Thr Asn Leu Val Ser
1               5

<210> SEQ ID NO 31
<211> LENGTH: 11
<212> TYPE: PRT
<213> ORGANISM: artificial
<220> FEATURE:
<223> OTHER INFORMATION: chemically synthesized
```

```
<400> SEQUENCE: 31

Gln Gly Gly Tyr Thr Ser Gly Asp Gly Ile Ala
1               5                   10

<210> SEQ ID NO 32
<211> LENGTH: 11
<212> TYPE: PRT
<213> ORGANISM: artificial
<220> FEATURE:
<223> OTHER INFORMATION: chemically synthesized

<400> SEQUENCE: 32

Gln Gly Ala Tyr Thr Ser Gly Asp Gly Ile Ala
1               5                   10

<210> SEQ ID NO 33
<211> LENGTH: 11
<212> TYPE: PRT
<213> ORGANISM: artificial
<220> FEATURE:
<223> OTHER INFORMATION: chemically synthesized

<400> SEQUENCE: 33

Gln Gly Gly Tyr Ser Ser Gly Asp Gly Ile Ala
1               5                   10

<210> SEQ ID NO 34
<211> LENGTH: 11
<212> TYPE: PRT
<213> ORGANISM: artificial
<220> FEATURE:
<223> OTHER INFORMATION: chemically synthesized

<400> SEQUENCE: 34

Gln Gly Gly Tyr Thr Ser Gly Glu Gly Ile Ala
1               5                   10

<210> SEQ ID NO 35
<211> LENGTH: 11
<212> TYPE: PRT
<213> ORGANISM: artificial
<220> FEATURE:
<223> OTHER INFORMATION: chemically synthesized

<400> SEQUENCE: 35

Gln Gly Gly Tyr Thr Ser Gly Asp Gly Leu Ala
1               5                   10

<210> SEQ ID NO 36
<211> LENGTH: 11
<212> TYPE: PRT
<213> ORGANISM: artificial
<220> FEATURE:
<223> OTHER INFORMATION: chemically synthesized

<400> SEQUENCE: 36

Gln Gly Gly Tyr Thr Ser Gly Asp Gly Ile Val
1               5                   10

<210> SEQ ID NO 37
<211> LENGTH: 11
<212> TYPE: PRT
<213> ORGANISM: artificial
<220> FEATURE:
<223> OTHER INFORMATION: chemically synthesized

<400> SEQUENCE: 37
```

```
Gln Gly Gly Phe Thr Ser Gly Asp Gly Ile Ala
1               5                   10

<210> SEQ ID NO 38
<211> LENGTH: 11
<212> TYPE: PRT
<213> ORGANISM: artificial
<220> FEATURE:
<223> OTHER INFORMATION: chemically synthesized

<400> SEQUENCE: 38

Gln Gly Gly Tyr Thr Thr Gly Glu Gly Ile Ala
1               5                   10

<210> SEQ ID NO 39
<211> LENGTH: 10
<212> TYPE: PRT
<213> ORGANISM: artificial
<220> FEATURE:
<223> OTHER INFORMATION: chemically synthesized

<400> SEQUENCE: 39

Gly Phe Ser Leu Ser Asn Tyr Val Leu Ala
1               5                   10

<210> SEQ ID NO 40
<211> LENGTH: 10
<212> TYPE: PRT
<213> ORGANISM: artificial
<220> FEATURE:
<223> OTHER INFORMATION: chemically synthesized

<400> SEQUENCE: 40

Gly Tyr Ser Leu Ser Asn Tyr Val Leu Ala
1               5                   10

<210> SEQ ID NO 41
<211> LENGTH: 10
<212> TYPE: PRT
<213> ORGANISM: artificial
<220> FEATURE:
<223> OTHER INFORMATION: chemically synthesized

<400> SEQUENCE: 41

Gly Phe Thr Leu Ser Asn Tyr Val Leu Ala
1               5                   10

<210> SEQ ID NO 42
<211> LENGTH: 10
<212> TYPE: PRT
<213> ORGANISM: artificial
<220> FEATURE:
<223> OTHER INFORMATION: chemically synthesized

<400> SEQUENCE: 42

Gly Phe Ser Leu Thr Asn Tyr Val Leu Ala
1               5                   10

<210> SEQ ID NO 43
<211> LENGTH: 10
<212> TYPE: PRT
<213> ORGANISM: artificial
<220> FEATURE:
<223> OTHER INFORMATION: chemically synthesized

<400> SEQUENCE: 43
```

Gly Phe Ser Leu Ser Asn Phe Val Leu Ala
1               5                   10

<210> SEQ ID NO 44
<211> LENGTH: 10
<212> TYPE: PRT
<213> ORGANISM: artificial
<220> FEATURE:
<223> OTHER INFORMATION: chemically synthesized

<400> SEQUENCE: 44

Gly Phe Ser Leu Ser Asn Tyr Val Ile Ala
1               5                   10

<210> SEQ ID NO 45
<211> LENGTH: 10
<212> TYPE: PRT
<213> ORGANISM: artificial
<220> FEATURE:
<223> OTHER INFORMATION: chemically synthesized

<400> SEQUENCE: 45

Gly Phe Ser Leu Ser Asn Tyr Val Leu Val
1               5                   10

<210> SEQ ID NO 46
<211> LENGTH: 12
<212> TYPE: PRT
<213> ORGANISM: artificial
<220> FEATURE:
<223> OTHER INFORMATION: chemically synthesized

<400> SEQUENCE: 46

Thr Ile Val Ser Gly Thr Thr Tyr Tyr Ala Ser Trp
1               5                   10

<210> SEQ ID NO 47
<211> LENGTH: 12
<212> TYPE: PRT
<213> ORGANISM: artificial
<220> FEATURE:
<223> OTHER INFORMATION: chemically synthesized

<400> SEQUENCE: 47

Thr Leu Val Ser Gly Thr Thr Tyr Tyr Ala Ser Trp
1               5                   10

<210> SEQ ID NO 48
<211> LENGTH: 12
<212> TYPE: PRT
<213> ORGANISM: artificial
<220> FEATURE:
<223> OTHER INFORMATION: chemically synthesized

<400> SEQUENCE: 48

Thr Ile Val Ser Gly Thr Ser Tyr Tyr Ala Ser Trp
1               5                   10

<210> SEQ ID NO 49
<211> LENGTH: 12
<212> TYPE: PRT
<213> ORGANISM: artificial
<220> FEATURE:
<223> OTHER INFORMATION: chemically synthesized

<400> SEQUENCE: 49

Thr Ile Val Ser Gly Thr Thr Tyr Tyr Val Ser Trp

```
<210> SEQ ID NO 50
<211> LENGTH: 12
<212> TYPE: PRT
<213> ORGANISM: artificial
<220> FEATURE:
<223> OTHER INFORMATION: chemically synthesized

<400> SEQUENCE: 50

Thr Ile Val Ser Gly Thr Thr Phe Tyr Ala Ser Trp
1               5                   10

<210> SEQ ID NO 51
<211> LENGTH: 12
<212> TYPE: PRT
<213> ORGANISM: artificial
<220> FEATURE:
<223> OTHER INFORMATION: chemically synthesized

<400> SEQUENCE: 51

Thr Ile Val Ser Gly Ser Thr Tyr Tyr Ala Thr Trp
1               5                   10

<210> SEQ ID NO 52
<211> LENGTH: 10
<212> TYPE: PRT
<213> ORGANISM: artificial
<220> FEATURE:
<223> OTHER INFORMATION: chemically synthesized

<400> SEQUENCE: 52

Gly Leu Pro His Phe Ile Thr Gly Asp Ile
1               5                   10

<210> SEQ ID NO 53
<211> LENGTH: 10
<212> TYPE: PRT
<213> ORGANISM: artificial
<220> FEATURE:
<223> OTHER INFORMATION: chemically synthesized

<400> SEQUENCE: 53

Gly Ile Pro His Tyr Ile Thr Gly Asp Ile
1               5                   10

<210> SEQ ID NO 54
<211> LENGTH: 10
<212> TYPE: PRT
<213> ORGANISM: artificial
<220> FEATURE:
<223> OTHER INFORMATION: chemically synthesized

<400> SEQUENCE: 54

Gly Leu Pro His Tyr Ile Thr Gly Asp Leu
1               5                   10

<210> SEQ ID NO 55
<211> LENGTH: 10
<212> TYPE: PRT
<213> ORGANISM: artificial
<220> FEATURE:
<223> OTHER INFORMATION: chemically synthesized

<400> SEQUENCE: 55

Gly Leu Pro His Tyr Leu Thr Gly Asp Ile
1               5                   10
```

```
<210> SEQ ID NO 56
<211> LENGTH: 10
<212> TYPE: PRT
<213> ORGANISM: artificial
<220> FEATURE:
<223> OTHER INFORMATION: chemically synthesized

<400> SEQUENCE: 56

Gly Leu Pro His Tyr Ile Thr Gly Glu Ile
1               5                   10

<210> SEQ ID NO 57
<211> LENGTH: 10
<212> TYPE: PRT
<213> ORGANISM: artificial
<220> FEATURE:
<223> OTHER INFORMATION: chemically synthesized

<400> SEQUENCE: 57

Gly Leu Pro Asn Tyr Ile Thr Gly Asp Ile
1               5                   10

<210> SEQ ID NO 58
<211> LENGTH: 10
<212> TYPE: PRT
<213> ORGANISM: artificial
<220> FEATURE:
<223> OTHER INFORMATION: chemically synthesized

<400> SEQUENCE: 58

Gly Leu Pro His Phe Ile Thr Gly Glu Ile
1               5                   10

<210> SEQ ID NO 59
<211> LENGTH: 13
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(13)
<223> OTHER INFORMATION: X1 is G, A, or V; X2 is S or T; X3 is S or T;
      X4 is M, L, S or V; X5 is Y or F; X6 is L or I; X7 is S or T.

<400> SEQUENCE: 59

Gln Xaa Xaa Gln Xaa Xaa Xaa Asn Asn Asn Gln Xaa Xaa
1               5                   10

<210> SEQ ID NO 60
<211> LENGTH: 7
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(7)
<223> OTHER INFORMATION: X, X2, X3 and X6 are T, Y, S, Q or N; and X4
      and X5 is G, A, V, L, I, M, P, F, W or C.

<400> SEQUENCE: 60

Gly Xaa Xaa Xaa Xaa Xaa Xaa
1               5

<210> SEQ ID NO 61
<211> LENGTH: 11
```

```
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(11)
<223> OTHER INFORMATION: X1, X2, X6 and X8, X9 and X10 are G, A, V, L,
      I, M, P, F, W or C; X3, X4 and X5 are T, Y, S, Q or N; X7 is D or
      E.

<400> SEQUENCE: 61

Gln Xaa Xaa Xaa Xaa Xaa Xaa Xaa Xaa Xaa
1               5                   10

<210> SEQ ID NO 62
<211> LENGTH: 10
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(10)
<223> OTHER INFORMATION: X1, X4, X8, X9 and X10 are G, A, V, L, M or I;
      X2 and X7 are F, W or Y; X3, X5 is T, Y, or S; and X6 is N or Q

<400> SEQUENCE: 62

Xaa Xaa Xaa Xaa Xaa Xaa Xaa Xaa Xaa Xaa
1               5                   10

<210> SEQ ID NO 63
<211> LENGTH: 12
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(12)
<223> OTHER INFORMATION: X1, X4, X6, X7 and X11 are T, S or Y; X2, X3 or
      X10, are G, A, V, L, M or I; X5 is G, V, A, L or I, X8 and X9 are
      F or Y, and X12 is W, Y or F.

<400> SEQUENCE: 63

Xaa Xaa Xaa Xaa Xaa Xaa Xaa Xaa Xaa Xaa Xaa Xaa
1               5                   10

<210> SEQ ID NO 64
<211> LENGTH: 10
<212> TYPE: PRT
<213> ORGANISM: artificial
<220> FEATURE:
<223> OTHER INFORMATION: chemically synthesized
<220> FEATURE:
<221> NAME/KEY: MISC_FEATURE
<222> LOCATION: (1)..(10)
<223> OTHER INFORMATION: X1, X2, X5 X7 and X9 are G, L, M, I, V, or A,
      X6 is T, S or Y, X8 is D or E, X3 is H, K or R, X4 is Y or F.

<400> SEQUENCE: 64

Xaa Xaa Pro Xaa Xaa Xaa Xaa Xaa Xaa Xaa
1               5                   10

<210> SEQ ID NO 65
<211> LENGTH: 330
<212> TYPE: DNA
<213> ORGANISM: rabbit

<400> SEQUENCE: 65
```

```
-continued caagtgctga cccagactcc atcccccgtg tctgcagctg tgggaggcac agtcaccatc      60
aattgccagg ccagtcaaag tgtttataat aacaaccaat tatcctggta tcagcagaaa     120
ccagggcagc ctcccaagct cctgatctat ggtacatcca atctggcatc tggggtccca     180
tcgcggttca aaggcagtgg atctgggaca cagttcactc tcaccatcag cagcgtgcag     240
tgtgacgatg ctgccactta ctactgtcaa ggcggttata ctagtggtga tggtattgct     300
ttcggcggag ggaccgaggt ggtcgtcaaa                                      330

<210> SEQ ID NO 66
<211> LENGTH: 345
<212> TYPE: DNA
<213> ORGANISM: rabbit

<400> SEQUENCE: 66
cagtcggtgg aggagtccgg gggtcgcctg gtcacgcctg gacacccct gacactcacc       60 tgcacagtct ctggattctc cctcagtaac tatgtattgg cctgggtccg ccaggctcca    120
gggaaggggc tggagtggat cggaaccatt gttagcggta ccacatacta cgcgagttgg    180
gcgaaaggcc gattcaccat ctccaaaacc tcgaccacgg tgcatctgaa aatcaccagt    240
ccgacaaccg aggacacggc cacctatttc tgtgtcagag gtttgcctca ttatattact    300
ggggacatct ggggcccagg caccctggtc accgtctcct taggg                    345
```

What is claimed is:

1. An isolated antibody having specific binding for THC and its metabolites, wherein said antibody comprises CDR amino acid sequences as follows: L1: QASQSVYNNNQLS (SEQ ID NO:1); L2: GTSNLAS (SEQ ID NO:2); L3: QGGYTSGDGIA (SEQ ID NO:3); H1: GFSLSNYVLA (SEQ ID NO:4); H2: TIVSGTTYYASW (SEQ ID NO:5); H3: GLPHYITGDI (SEQ ID NO:6); or homologous amino acid sequences having at least 85% homology thereto.

2. The antibody of claim 1, wherein the amino acid sequence for the light chain variable region comprises the sequence: QVLTQTPSPVSAAVGGTVTINCQASQS-VYNNNQLSWYQQKPGQPPKLLIYGTSNLAS GVPSR-FKGSGSGTQFTLTISSVQCDDAATYYC-QGGYTSGDGIAFGGGTEVVVK (SEQ ID NO:7), or homologous amino acid sequences having at least 85% homology thereto.

3. The antibody of claim 1, wherein the amino acid sequence for the heavy chain variable region comprises the sequence: QSVEESGGRLVTPGTPLTLTCTVSGFSL-SNYVLAWVRQAPGKGLEWIGTIVSGTTYY ASWAKGRFTISKTSTTVHLKITSPTTED-TATYFCVRGLPHYITGDIWGPGTLVTVSLG (SEQ ID NO:8), or homologous amino acid sequences having at least 85% homology thereto.

4. The antibody of claim 1, wherein the antibody is a monoclonal antibody.

5. The monoclonal antibody of claim 4, wherein the antibody is produced by recombinant methods or by a hybridoma.

6. The monoclonal antibody of claim 4, wherein the antibody is a rabbit antibody.

7. A host cell expressing the antibody of claim 1.

8. The host cell of claim 7, wherein the host cell is a HEK 293 cell.

9. An immunoassay for detecting the presence of THC and its metabolites in a sample, comprising
   contacting the sample with the antibody of claim 1, such that immune complexes form between the antibody and THC or its metabolites;
   detecting and relating the binding of the antibody to the THC or its metabolites to the presence of said THC or its metabolites in the sample.

10. The immunoassay of claim 9, wherein the antibody is labeled or conjugated to particles.

11. A lateral flow immunoassay strip for detecting the presence of THC and/or its metabolites in a fluid sample, comprising a membrane strip coated with a THC-protein conjugate on a test line, and particles coated with the antibody of claim 1.

12. A method for detecting the presence of THC in a sample, comprising the steps of
   (1) providing the lateral flow immunoassay strip of claim 11;
   (2) contacting said lateral flow immunoassay strip with a sample to be tested for the presence of $\Delta^9$-THC in the sample;
   (3) allowing the sample to migrate along the strip;
   (4) determining whether the immunoassay is positive or negative for the presence of $\Delta^9$-THC in the sample by detecting the presence or absence of the antibody-coated particles in the test line region of the lateral flow immunoassay strip.

13. A kit for testing for the presence of THC in saliva, comprising the lateral flow immunoassay strip for THC of claim 11, and instructions for performing the test.

* * * * *